(12) United States Patent
Zhao et al.

(10) Patent No.: US 6,306,975 B1
(45) Date of Patent: Oct. 23, 2001

(54) RADIATION-GRAFTED SOLID SUPPORTS FOR CHEMICAL SYNTHESIS

(75) Inventors: Chanfeng Zhao, San Diego; John E. Lillig, Poway; Robert Neeper, Lakeside; Gordon W. Hudson, Vista; Anthony W. Czarnik; Zahra Parandoosh, both of San Diego; Gary S. David, La Jolla; Xiao-Yi Xiao, San Diego, all of CA (US)

(73) Assignee: Irori, San Diego, CA (US)

( * ) Notice: Subject to any disclaimer, the term of this patent is extended or adjusted under 35 U.S.C. 154(b) by 0 days.

(21) Appl. No.: 09/010,951

(22) Filed: Jan. 22, 1998

Related U.S. Application Data

(63) Continuation-in-part of application No. 08/958,254, filed on Oct. 7, 1997, which is a continuation-in-part of application No. 08/912,998, filed on Aug. 11, 1997, which is a continuation-in-part of application No. 08/826,253, filed on Mar. 27, 1997, which is a continuation-in-part of application No. 08/788,594, filed on Jan. 23, 1997, now abandoned, which is a continuation-in-part of application No. 08/857,800, filed on Jan. 22, 1997.

(51) Int. Cl.[7] ............................ C08F 259/00; C08F 8/00; C08L 33/02; C08G 63/48
(52) U.S. Cl. ................................ 525/276; 525/7; 525/7.1; 525/8; 525/10; 525/11; 525/32.1; 525/32.2; 525/33; 525/50; 525/54.3; 525/55; 525/63; 525/64; 525/69; 525/70; 525/78
(58) Field of Search ............................ 525/7, 7.1, 8, 10, 525/11, 32.1, 32.2, 3, 50, 54.33, 55, 63, 64, 69, 70, 78, 276

(56) References Cited

U.S. PATENT DOCUMENTS

| | | | |
|---|---|---|---|
| 3,390,067 | 6/1968 | Miller et al. | 204/159.17 |
| 4,340,057 | 7/1982 | Bloch et al. | 128/284 |
| 4,506,035 | 3/1985 | Barnett et al. | 521/53 |
| 4,602,045 | 7/1986 | Markus et al. | 521/27 |
| 4,661,383 | 4/1987 | Elsenbaumer et al. | 427/302 |
| 4,699,966 | 10/1987 | Harris et al. | 528/12 |
| 4,954,256 | 9/1990 | Degen et al. | 210/490 |
| 5,037,667 | 8/1991 | Dubrow et al. | 427/44 |
| 5,232,600 | 8/1993 | Degen et al. | 210/640 |
| 5,304,404 | 4/1994 | Morra et al. | 427/512 |
| 5,376,400 | 12/1994 | Goldberg et al. | 427/2.24 |
| 5,576,106 | 11/1996 | Kerbow et al. | 428/403 |

OTHER PUBLICATIONS

Chappas et al., "The effect of acid on the radiation–induced grafting of styrene to polyethylene," *Radiat. Phys. Chem.*, (1979), pp. 847–852, 14.

Dilli, et al., "Effect of acid on the radiation–induced copolymerization of monomers to cellulose," *Polymer Letters Edition*, (1973), pp. 711–715, 11.

Feinberg et al., "Zinc chloride–catalyzed chloromethylation of resins for solid phase peptide synthesis," *Tetrahedron*, (1974), pp. 3209–3212, 30.

Garnett, et al., "Acid effects in the styrene comonomer technique for radiation grafting to wool," *Polymer Letters Edition*, (1977), pp. 421–425, 15.

Li et al., "Kinetic comparison of Amide formation on various cross–linked polystyrene resins," *J. Comb. Chem.*, (1998)—American Chem. Soc. Website, 10.1021/cc9800201.

Wilson and Czarnik, Combinatorial Chemistry, John Wiley & Sons, Inc., 1997, Chapter 6, "Solid–Phase Methods in Combinatorial Chemistry", pp. 119–131.

Zhao et al., "Polystyrene grafted fluoropolymer microtubes: New supports for solid–phase organic synthesis with useful performance at high temperature," *J. Com. Chem.*, (1999), pp. 91–95, 1.

*Primary Examiner*—Ardin H. Marschel
(74) *Attorney, Agent, or Firm*—Kilpatrick Stockton LLP

(57) ABSTRACT

Methods for irradiation induced graft polymerization of a monomers, such as styrenes, onto fluoropolymers are provided. The methods, which involve either the use of acids, preferably mineral acids, or creating a rough surface on the fluoropolymer, provide higher levels of grafting of the copolymer than grafting in the absence of the acid or of the rough surface on the fluoropolymer. Also provided are grafted copolymers produced by the methods. Methods for increasing the performance of solid phase assays, such as scintillation proximity assays, are also provided.

13 Claims, 9 Drawing Sheets

RADIATION-GRAFTED SOLID SUPPORTS FOR CHEMICAL SYNTHESIS

RELATED APPLICATIONS

For any U.S. National Stage purposes this application is a continuation-in-part of U.S. application Ser. No. 08/958,254, entitled filed Oct. 7, 1997, which is a continuation-in-part of U.S. application Ser. No. 08/912,998, entitled filed Aug, 11, 1997, which is a continuation-in-part of U.S. application Ser. No. 08/826,253, entitled filed Mar. 27, 1997, which is a continuation-in-part of U.S. application Ser. No. 08/788,594, now abandoned, both entitled filed Jan. 23, 1997. This application is also a continuation-in-part of U.S. application Ser. No. 08/857,800, filed Jan. 22, 1997.

For international purposes priority to each of the above-noted applications is claimed herein. Where permitted, the subject matter of each of above-noted U.S. applications is incorporated herein by reference in its entirety.

FIELD OF THE INVENTION

The present invention relates to methods for radiation grafting monomers onto polymeric surfaces and the resulting grafted surfaces are provided. In particular, the methods involve performing radiation grafting onto a fluoropolymer in the presence of an acid, preferably a mineral acid, and/or creating a rough surface on the fluoropolymer prior to radiation grafting. The resulting grafted materials are also provided.

BACKGROUND OF THE INVENTION

Drug Discovery

Drug discovery relies on the ability to identify compounds that interact with a selected target, such as a cell, an antibody, receptor, enzyme, transcription factor or the like. Traditional drug discovery relied on collections or "libraries" obtained from proprietary databases of compounds accumulated over many years, natural products, fermentation broths, and rational drug design. Recent advances in molecular biology, chemistry and automation have resulted in the development of rapid, high throughput screening (HTS) protocols to screen these collections. In connection with HTS, methods for generating molecular diversity and for detecting, identifying and quantifying biological or chemical material have been developed. These advances have been facilitated by fundamental developments in chemistry, including the development of highly sensitive analytical methods, solid state chemical synthesis, and sensitive and specific biological assay systems.

Analyses of biological interactions and chemical reactions, however, require the use of labels or tags to track and identify the results of such analyses. Typically biological reactions, such as binding, catalytic, hybridization and signaling reactions, are monitored by labels, such as radioactive, fluorescent, photoabsorptive, luminescent and other such labels, or by direct or indirect enzyme labels. Chemical reactions are also monitored by direct or indirect means, such as by linking the reactions to a second reaction in which a colored, fluorescent, chemoluminescent or other such product results. These analytical methods, however, are often time consuming, tedious and, when practiced in vivo, invasive. In addition, each reaction is typically measured individually, in a separate assay. There is, thus, a need to develop alternative and convenient methods for tracking and identifying analytes in biological interactions and the reactants and products of chemical reactions.

Combinatorial Libraries

The provision and maintenance of compounds to support HTS have become critical. New methods for the lead generation and lead optimization have emerged to address this need for diversity. Among these methods is combinatorial chemistry, which has become a powerful tool in drug discovery and materials science. Methods and strategies for generating diverse libraries, primarily. peptide- and nucleotide-based oligomer libraries, have been developed using molecular biology methods and/or simultaneous chemical synthesis methodologies (see, e.g., A Practical Guide to Combinatorial Chemistry, DeWitt, S. H. (1997) Czarnik, A. W., Editors, ACS Books, Washington; Combinatorial Chemistry: Synthesis and Application, Wilson, S. H. (1997) Czarnik, A. W., Editors, Wiley & Sons, NY, N.Y.; Dower et al. (1991) *Annu. Rep. Med. Chem.* 26:271–280; Fodor et al. (1991) *Science* 251:767–773; Jung et al. (1992) *Angew. Chem. Ind. Ed. Engl.* 31:367–383; Zuckerman et al. (1992) *Proc. Natl. Acad. Sci. USA* 89:4505–4509; Scott et al. (1990) *Science* 249:386–390; Devlin et al. (1990) *Science* 249:404–406; Cwirla et al. (1990) *Proc. Natl. Acad. Sci. USA* 87:6378–6382; and Gallop et al. (1994) *J. Medicinal Chemistry* 37:1233–1251). The resulting combinatorial libraries potentially contain millions of pharmaceutically relevant compounds and that can be screened to identify compounds that exhibit a selected activity.

High Throughput Screening

In addition, exploitation of this diversity requires development of methods for rapidly screening compounds. Advances in instrumentation, molecular biology and protein chemistry, and the adaptation of biochemical activity screens into microplate formats, has made it possible to screen of large numbers of compounds. Also, because compound screening has been successful in areas of significance for the pharmaceutical industry, high throughput screening (HTS) protocols have assumed importance. Presently, there are hundreds of HTS systems operating throughout the world, which are used, not only for compound screening for drug discovery, but also for immunoassays, cell-based assays and receptor-binding assays.

An essential element of high throughput screening for drug discovery process and areas in which molecules are identified and tracked, is the ability to extract the information made available during synthesis and screening of a library, identification of the active components of intermediary structures, and the reactants and products of assays. While there are several techniques for identification of intermediary products and final products, nanosequencing protocols that provide exact structures are only applicable on mass to naturally occurring linear oligomers such as peptides and amino acids. Mass spectrographic (MS) analysis is sufficiently sensitive to determine the exact mass and fragmentation patterns of individual synthesis steps, but complex analytical mass spectrographic strategies are not readily automated nor conveniently performed. Also, mass spectrographic analysis provides at best simple connectivity information, but no stereoisomeric information, and generally cannot discriminate among isomeric monomers. Another problem with mass spectrographic analysis is that it requires pure compounds; structural determinations on complex mixtures is either difficult or impossible. Finally, mass spectrographic analysis is tedious and time consuming. Thus, although there are a multitude of solutions to the generation of libraries and to screening protocols, there are no ideal solutions to the problems of identification, tracking and categorization.

These problems arise in any screening or analytical process in which large numbers of molecules or biological entities are screened. In any system, once a desired molecule(s) has been isolated, it must be identified. Simple means for identification do not exist. Because of the problems inherent in any labeling procedure, it would be desirable to have alternative means for tracking and quantitating chemical and biological reactions during synthesis and/or screening processes, and for automating such tracking and quantitating.

Solid Supports

A key feature in the use of combinatorial chemistry and high throughput screening in drug discovery is the solid support used during synthesis of the libraries. Such supports take a variety of forms, including, but not limited to, inorganics, natural polymers, and synthetic polymers, including, but not limited to: cellulose, cellulose derivatives, acrylic resins, glass that is derivatized to render it suitable for use a support, silica gels, polystyrene, gelatin, polyvinylpyrrolidone, copolymers of vinyl and acrylamide, polystyrene cross-linked with divinylbenzene or the like (see, Merrifield *Biochemistry* 1964, 3, 1385–1390), polyacrylamides, latex gels, dextran, rubber, silicon, plastics, nitrocellulose, natural sponges, metals, plastic, cross-linked dextrans, such as those sold under the tradename Sephadex (Pharmacia) and agarose gel, such as gels sold under the tradename Sepharose (Pharmacia), which is a hydrogen bonded polysaccharide-type agarose gel.

Radiation grafting of monomers allows a diversity of surface characteristics to be generated on polymeric supports (see, e.g., Maeji et al. (1994) *Reactive Polymers* 22:203–212; and Berg et al. (1989) *J. Am. Chem. Soc.* 111:8024–8026). For example, radiolytic grafting of monomers, such as vinyl monomers, or mixtures of monomers, to polymers, such as polyethylene and polypropylene, produce composites that have a wide variety of surface characteristics. These methods have been used to graft polymers to insoluble supports, particularly polypropylene, for synthesis of peptides and other molecules. These methods have not been successfully employed for fluoropolymers.

It is important for the supports to be resistant to the conditions in which syntheses and/or assays are performed. Consequently, fluoropolymeric materials for use as resins and solid supports, which are highly inert materials that are resistant to solvents and temperatures employed during synthesis would be widely employed in combinatorial chemistry. The disadvantage in using these polymers, however, is the difficulty encountered in binding or covalently bonding a substrate of interest because of their inert character. In combinatorial synthesis, the solid supports generally must possess functionality or be derivatized in such a way as to be able to covalently or otherwise bind a substrate of interest during the combinatorial synthesis. Typical functional groups include alcohols, amines, alkyl halides, phenols, aldehydes, nitriles, carboxyl groups and the like. Thus, in order to use highly inert fluoropolymeric resins as solid supports in combinatorial chemistry, the resins must be derivatized to allow for binding of a substrate of interest. The methods available for grafting polymers to fluoropolymers yield fluoropolymers in which the copolymer level of grafting is not sufficient to render the resulting surfaces suitable for use in synthesis and/or screening assays.

Therefore, it is an object herein to provide methods for irradiation induced graft polymerization that provide graft polymers of sufficiently high level of grafting such that the resulting grafted polymer (composite material) is suitable for use as a support in syntheses and screening, particularly for in combinatorial synthetic and high throughput screening protocols. It is also an object herein to provide the graft copolymers produced by the methods.

SUMMARY OF THE INVENTION

Methods for radiation grafting of monomers to polymers, particularly fluoropolymers, including fluoroelastomers, are provided. These methods result in higher levels of grafted polymers, particularly composite fluoropolymers, than heretofore had been achieved. The resulting composites are, thus, suitable for applications that require high density grafts. These applications include chemical syntheses and screening. Thus, methods for increasing the level of grafting of polymer on surfaces and methods for effectively grafting fluoropolymers, particularly PTFE and ETFE (ethylene-tetrafluoroethylene copolymer) surfaces are provided. The methods, particularly when used in combination, increase the level of grafting by about 5–400%, often 10–300% and usually at least about 20–200%, and particularly at least about 50%. In particular, the resulting radiation grafted fluoropolymers exhibit a level of grafting is greater than about 10 mg of graft per 320 mm$^2$, typically greater than 15 mg/320 mm$^2$, surface area of the fluoropolymer.

The resulting grafted composite polymers, particularly fluoropolymers are provided. Fluoropolymers intended as substrates for grafting, include, but are not limited to: PTFE (polytetrafluoroethylene, TEFLON®), ETFE (ethylene-tetrafluoroethylene copolymer, TEFZEL®), ECTFE (ethylene chlorotrifluoroethylene, HALAR®), PCTFE (polychlorotrifluoroethylene), PVF (polyvinyl fluoride), PVDF (polyvinylidene fluoride, HYLAR®), FEP (polyperfluoroethylene/propylene copolymer, FEP TEFLON®), PFA (tetrafluoroethylene-perfluoroalkyl-vinylether copolymer), HFP (hexafluoropropylene) and PPVE (perfluoropropyl vinyl ether) is provided herein.

The methods provided herein concomitantly increase the level of grafting of monomers and the loading of molecules and biological particles of interest on the resulting composites, which can be derivatized for subsequent linkage. These molecules, include, but are not limited to, macromolecules and small molecule substrates, on the resulting grafted polymer or the subsequently derivatized grafted polymer. In particular, increases in loading on the order of greater than about 10%, generally on the order of greater than about 30%, and often greater than about 50% are observed. Much larger increases in loading and/or the level of grafting (e.g., 300%) have been observed.

In one method provided herein, the grafting to the fluoropolymer or fluoroelastomer is increased by including an acid, preferably a mineral acid, such as sulfuric acid and nitric acid (typically at concentrations of from about 0.01–0.5 M) in the grafting mixture during irradiation.

Another method for increasing the level of grafting is also provided. This method increases the level of grafting not only on fluoropolymers, but also on other polymers, such as polyethylene. In this method, the polymer is treated prior to grafting to produce a roughened surface. This rough surface may be produced by any method known to those of skill in the art. While not being bound by any theory, the roughened surface possesses an increased level of porosity relative to standard fluoropolymer surfaces, and exhibits an increased level of grafting in the subsequent reaction. In preferred embodiments, the processes for producing the rough surface include machining, such as lathing, and the use of a mold which produces a desired rough surface. Mold cavities, which may be used to prepare the polymer, particularly the fluoropolymer, may be produced by processes such as electric discharge machining (EDM) or chemical etching. EDM typically involves conducting electricity from the item to be machined, in the present case the mold for the polymer onto which grafting is desired, preferably a fluoropolymer, through a dielectric fluid to an electrode. In this way, material is eroded away from the item being machined. Common to all methods are a resulting surface that feels rough to the touch compared to untreated surfaces. These methods are particularly suitable for use with fluoropolymers for which it had heretofore been difficult to obtain high loading on the resulting grafted surfaces. It may also be employed in combination with other methods, such as those set forth in U.S. Pat. Nos. 4,506,035, 4,602,045, 4,954,256, 5,229,172, 5,232,600, 5,376,400, 5,576,106 and 5,587,208, for radiation grafting of fluoropolymers. The resulting grafted surfaces will exhibit a greater amount of polymer grafted compared to the method in the absence of this treatment.

Methods that combine both roughening and inclusion of acid during the grafting reaction are provided. The combination of both methods results in a further increase in the amount of polymer grafted. The combination of both are particularly suitable for fluoropolymers. In such methods, the surfaces are roughened, such as by machining is used prior to grafting, and an acid, preferably a mineral acid, is added during the grafting process, is also provided.

The resulting radiation grafted material (matrix material) is used in any application in which radiation grafted material is used. Such methods, include, but are not limited to solid phase syntheses of macromolecules, small molecules and screening assays. The resulting material may be shaped or formed into any desired configuration for use in the selected application. The material may be formed as particles as small as 50 $\mu$m -about 200 $\mu$m or less or as large as needed. It may be formed into hollow containers, tubes, beads, balls, parallelepiped and so on. Of particular interest herein are hollow conformations in which the outer or inner or both surfaces, preferably the outer surface, are grafted.

In a preferred embodiment herein, the resulting composite polymers are formed into a desired shape, and are then used in combination with a memory, such as a recording device (i.e., a remotely programmable read/write or precoded memory) which is encased or embedded in the fluoropolymeric material, or with an engraved or imprinted symbology. Memories include optical memories, such as a 3-D optical memory or the 2-D optical bar codes provided herein, incorporated into the material or attached to the surface or engraved thereon. These devices are herein referred to generally as matrices with memories, and also are referred to as microreactors. The memories are used for identifying linked molecules or biological particles either by encoding the identity into the memory or associating the information, typically precoded, in the memory with identifying information in a database, typically using a computer.

In certain embodiments, the tubular devices are designed to serve as a reaction "flask", storage vial, or microtiter plate well. This is effected by having the tube differentially loaded and/or include different materials in the grafted coating so that linked moieties are differentially cleaved or differentially loaded. For example, one part of the tube includes a scintillant, but can be designed or grafted in such a manner that it is lightly loaded; another part is loaded with as much compound as possible. For example, relatively very long tubes (centimeters in length, for example about 1–3 cm) or other convenient shapes, such as star shaped or other shape from which pieces can be conveniently removed, are provided. The tag is inserted or a bar code is located at one end.

After synthesis, small (millimeter) pieces can be cut off the other end and put in various assays, or the product cleaved into a microplate well. In other embodiments, the tube may be relatively long or relatively large and of any geometry but coated uniformly. In these embodiments, the microreactor becomes a permanent or semi-permanent storage and information device for the compounds linked thereto, and is stored as such. Any time material is required for an assay, a piece of the tube can be cut off and tested.

The devices may also be formed from a ball or other shape with a screw cap or with other type of cap to permit access to the inside, or may be hollow and of such size or geometry to retain a memory inside or include an optical memory or symbology. These types of memories with matrices are, for example, polypropylene or fluoropolymer tubes with a radiation grafted functionalized polystyrene surface, produced by the methods herein, that completely enclose a selected memory, such as an radiofrequency (RF) tag. The surface may also or alternatively include an identifying symbology. Syntheses are performed on the functionalized surface, which is preferably polystyrene that can be derivatized where needed with a suitable moiety. These devices provide a means of solid phase chemistry without the need to load solid phase resins.

In certain embodiments, the combination of matrix with memory is used by contacting it with, linking it to, or placing it in proximity with a molecule or biological particle, such as a virus or phage particle, a bacterium or a cell, to produce a second combination of a matrix with memory and a molecule or biological particle. Identifying information is either stored in the memory or associated with information in the memory and stored in a remote database.

In certain embodiment, the combinations of matrix with memory or combination of matrix with memory and molecule or biological particle may be prepared when used or may be prepared before use and packaged or stored as such for futures use.

In certain embodiments, luminescent moieties, such as fluorophores, scintillants and other such compounds may also be incorporated into the surface or linked thereto. The resulting devices are used in assays, such as scintillation proximity assays and HTRF (homogeneous time-resolved fluorescence) assays.

A method for increasing the signal to noise (S/N) ratio achieved in assays using radiation grafted solid supports, particularly, but not exclusively, the supports provided herein, is also provided. In particular, washing the grafted material, following the preparation thereof in PBS (phosphate buffered saline) containing a detergent, particularly SDS (sodium dodecyl sulfate), preferably about 0.75% SDS, and preferably including charcoal, preferably about 35%, for about an extended time, typically about 1–2 days, significantly improved the signal/noise ratio in subsequent assays, such as scintillation proximity assays. Increases in signal to noise ratios of 2/1 to 47/1 have been observed. Such improvement should be observed with any solid support. Thus, a method for increasing the performance of assays on solid supports by washing the solid support with the linked biological particle(s) or molecule(s) with PBS containing from about 0.5 to 1.5% detergent, preferably SDS with or without charcoal, preferably about 15% to 50%, preferably about 35% by weight, for about two days is provided.

A, B, C . . . represent the chemical building blocks; a, b, c . . . represent the codes stored in memory that correspond to each of A, B, C, . . . , respectively. $S_a$, $S_b$, $S_c$ . . . represent respective signals sent to memory. Alternatively, the matrix supports have a precoded memory or are encoded with a symbology associated with information stored in a remote memory, such as a computer. The symbology, as well as the memory, may be precoded or encoded prior to or during synthesis.

Figure 1:
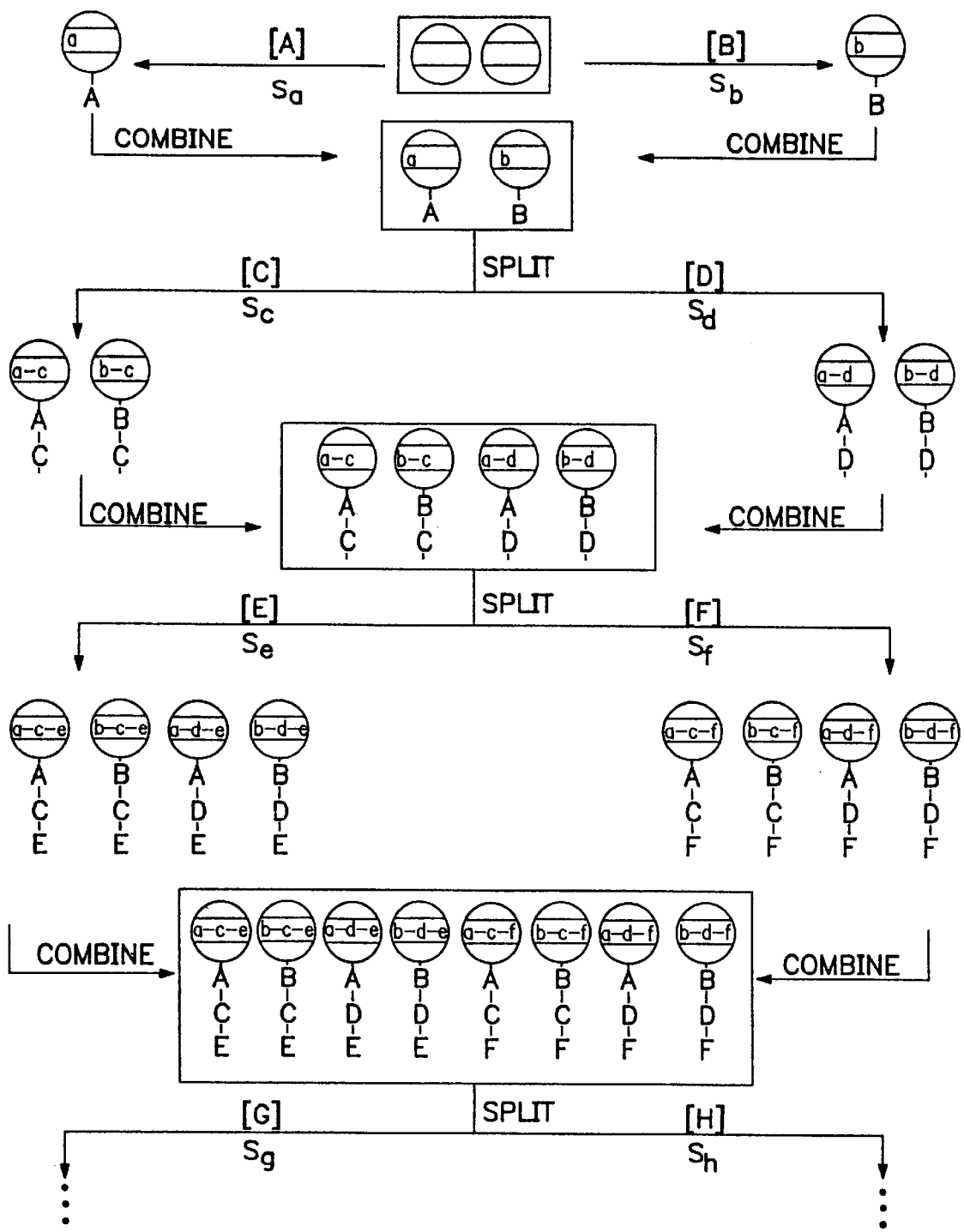
FIG. 1 depicts combinatorial synthesis of chemical libraries on the matrix supports with memories provided herein.
Figure 2:
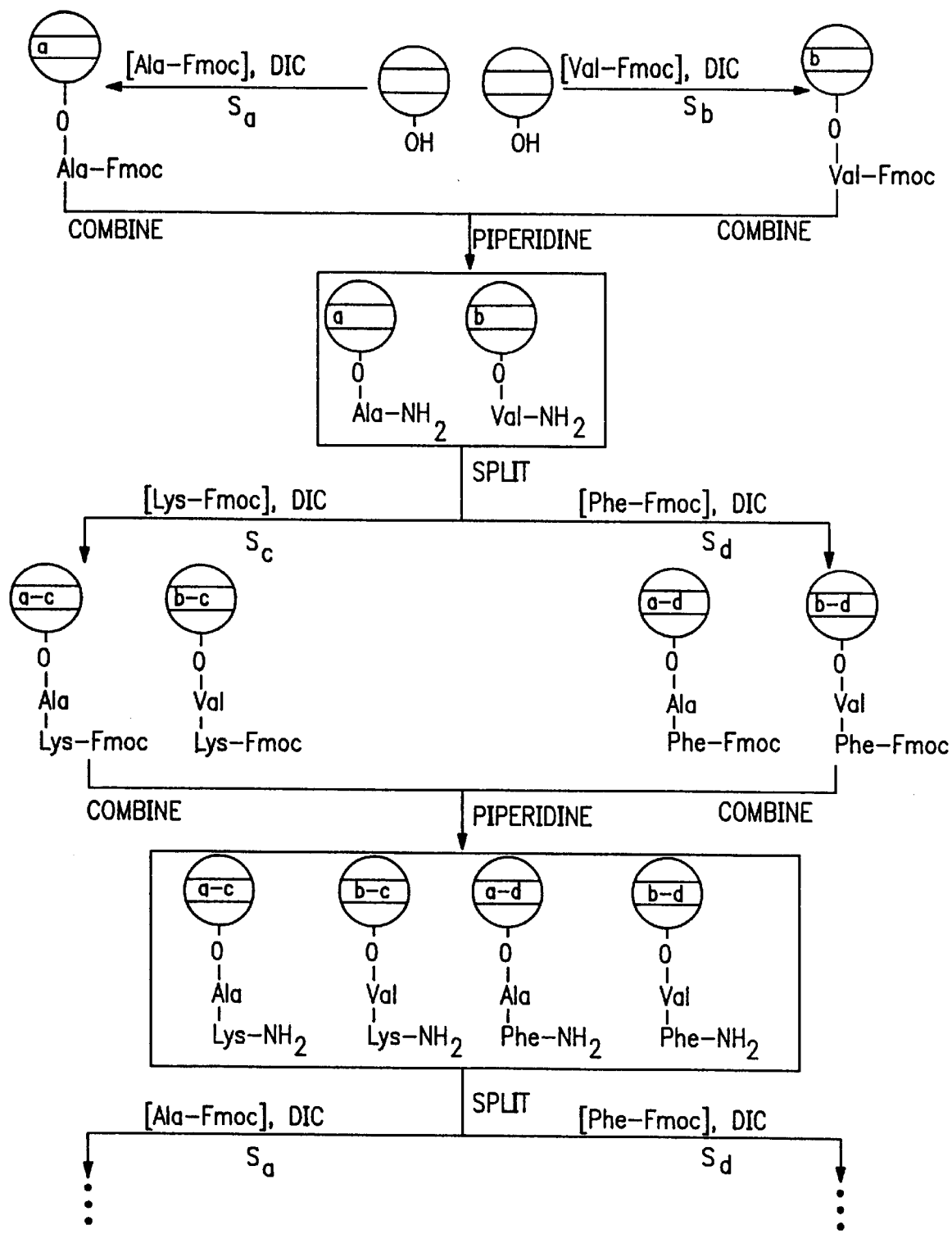

FIG. 2 depicts combinatorial synthesis of peptides on a matrix with memory prepared as described herein. Each amino acid has a corresponding code, a,b, c . . . , in the matrix memory, and L represents a Linker between the memory device and the pharmacophore. Again as in FIG. 1, the matrix supports may be engraved with a code or symbology associated with information stored in a remote memory.

Figure 3:
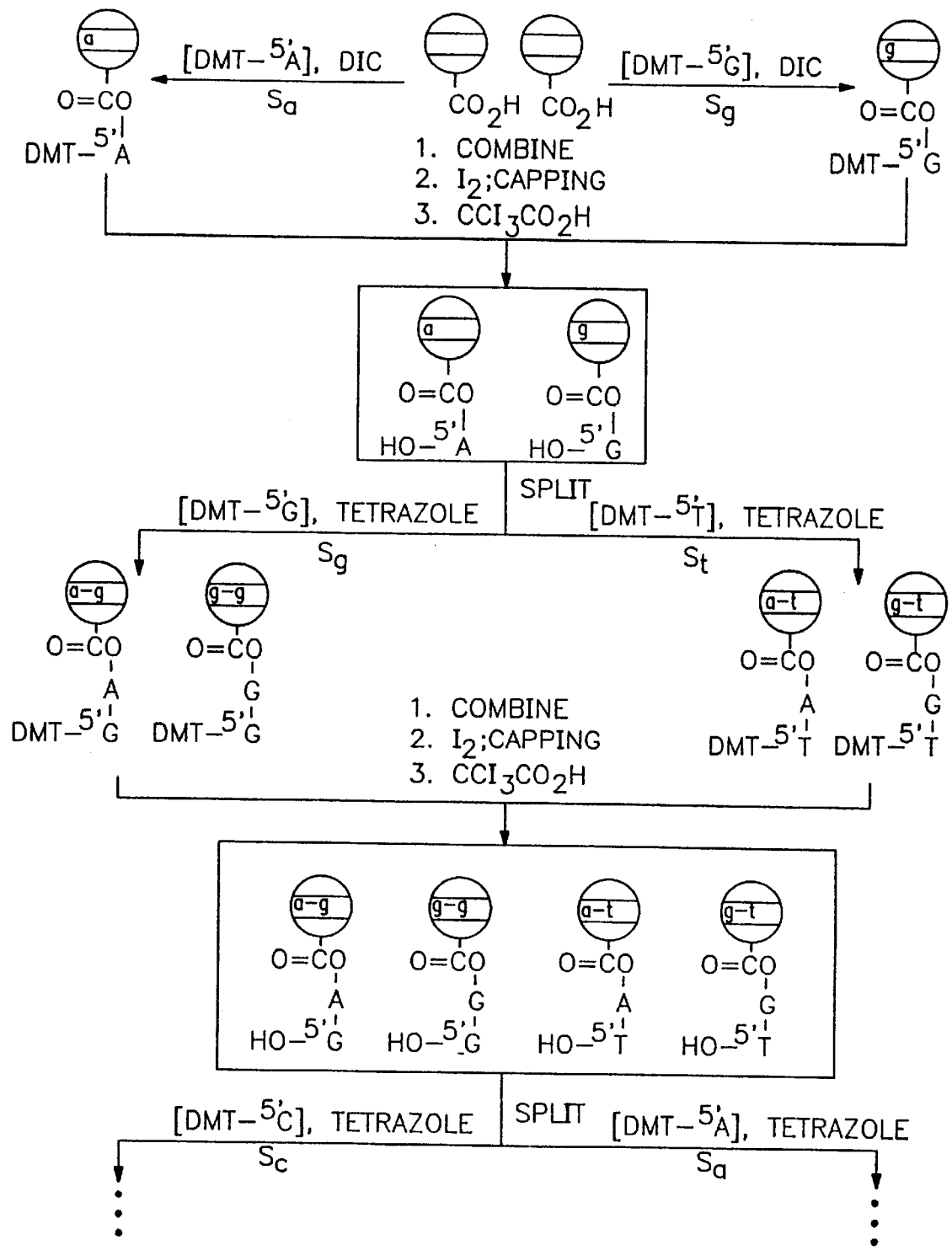

FIG. 3 depicts combinatorial synthesis of oligonucleotides on the matrix supports with memories. A, G, T and C represent nucleotides, and a, g, t, and c represent the electronic codes stored in memory that correspond to each of A, G T and C, respectively. The phosphoramidite method of oligonucleotide synthesis is performed by methods known to those of skill in the art (see, e.g., Brown et al. (1991) "Modern machine-aided methods of oligodeoxyribonucleotide synthesis" in Oligonucleotides Analogues EDITOR: Eckstein, Fritz (Ed), IRL, Oxford, UK., pp. 1–24, esp. pp. 4–7). As in FIGS. 1 and 2, the matrix may alternatively, or additionally, have symbology engraved thereon.

Figure 4:
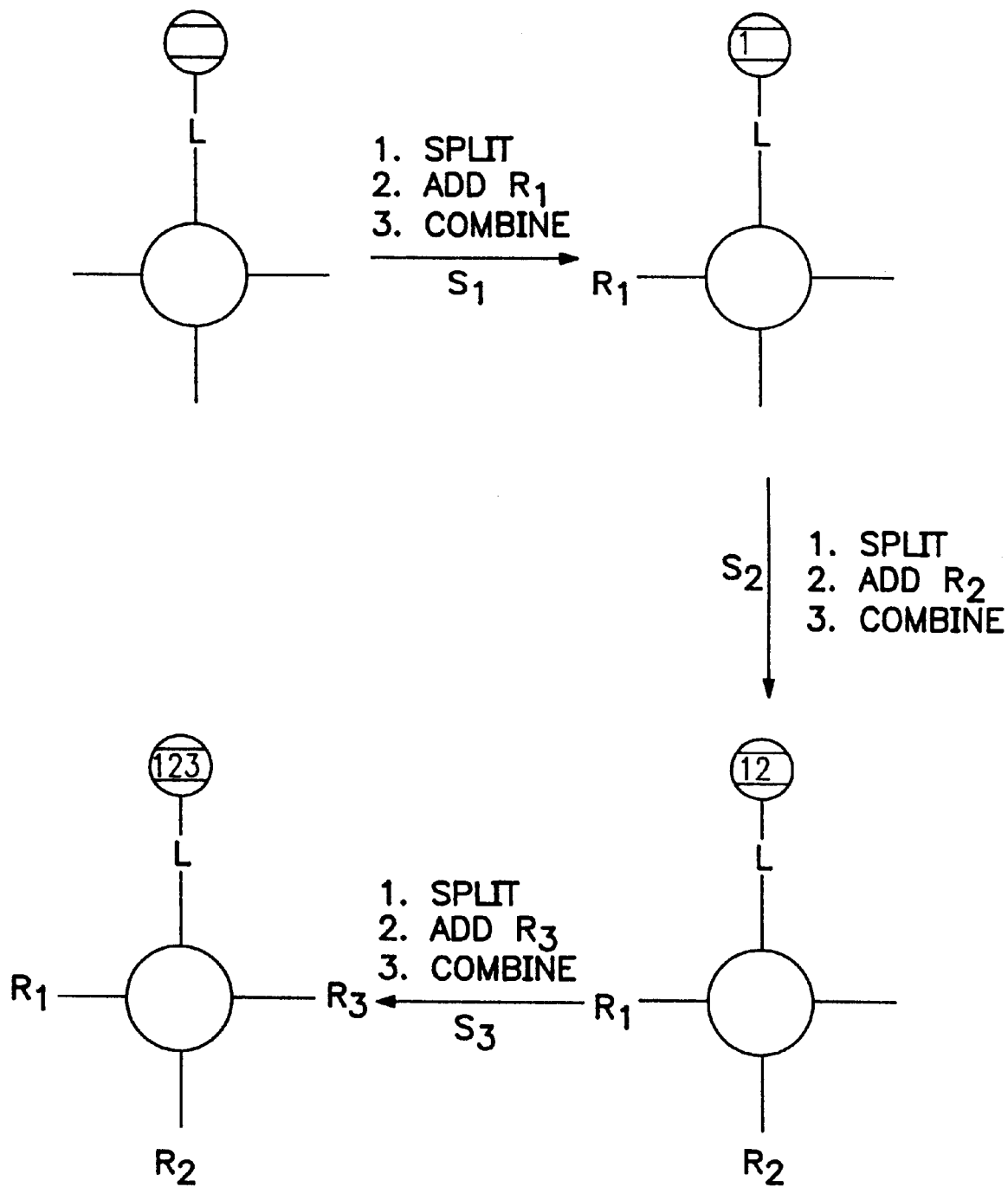

FIG. 4 depicts generation of a chemical library, such as a library of organic molecules, in which $R_1$, $R_2$ and $R_3$ are substituents on selected molecule, such as a pharmacophore monomer, each identified with a different signal, depicted as 1, 2 or 3, from the classes $S_1$, $S_2$ and $S_3$, respectively. The circle represents an organic pharmacophore. If $R_1$–$R_3$ are the same, and selected from among the same 50 choices, then the complete library contains $50^3=125,000$ members. If $R_1$–$R_3$ selected from among different sets of choices, then the resulting library has correspondingly more members. Each optical memory device can be encoded with information that represents the $R_n$ added and class ($S_n$) thereby providing a unique code for each library member. As in FIGS. 1–3, the matrix may be engraved with symbology, such as a two-dimensional bar code andlor include an electronic memory.

Figure 5:
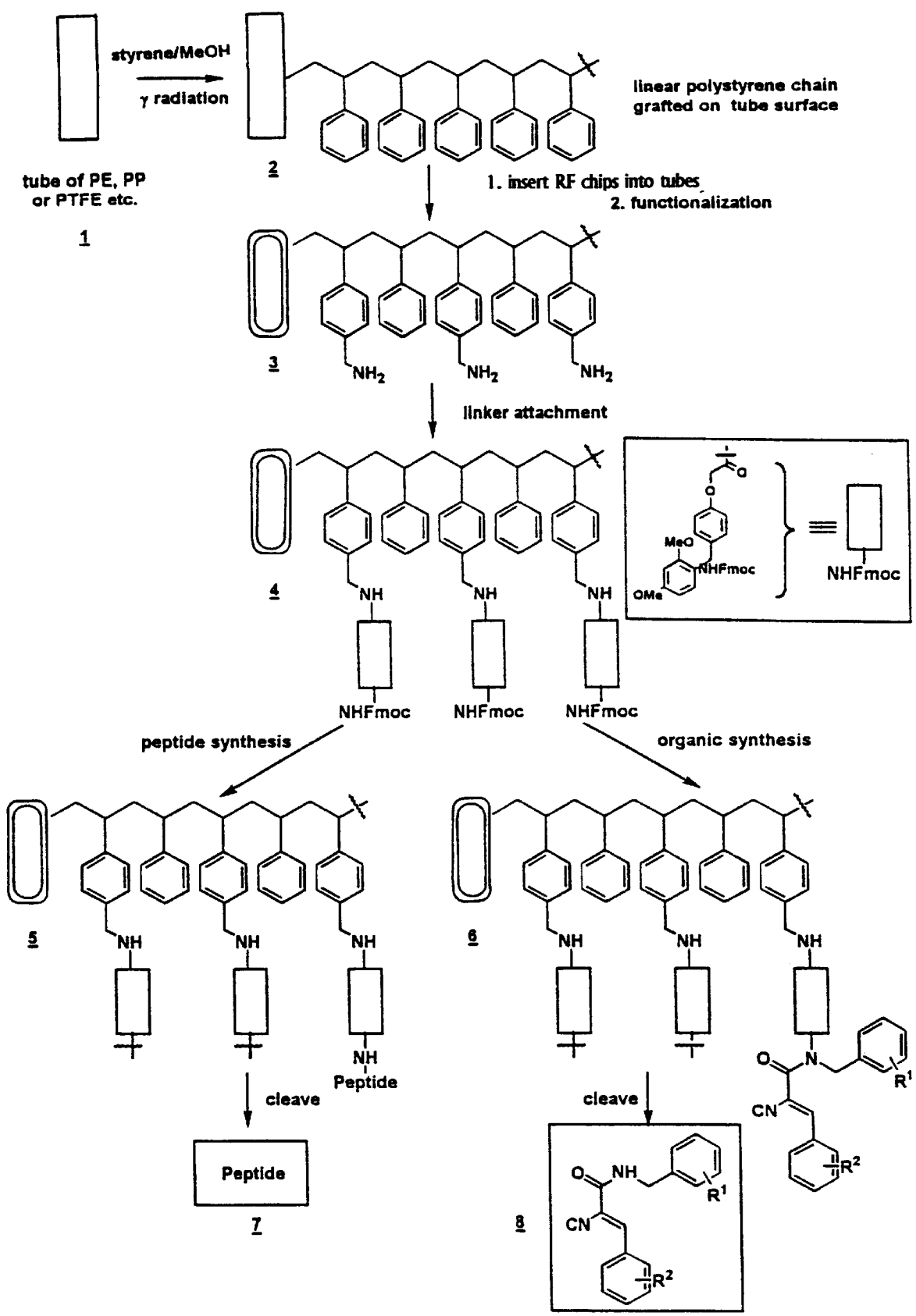

FIG. 5 shows the preparation and use of an exemplary tubular microreactor in which a surface, preferably the outer surface, is radiation grafted with monomers as described herein, and, if necessary adapted, such as by derivatization or otherwise activated, for use as a support matrix. As with the supports and "beads", these "beads" will include either an electromagnetically programmable (precoded or encodable) memory, or an optical memory on the surface, such as the 2-D optical bar code provided herein, or combinations thereof.

FIG. 6 depicts a protocol for radiation grafting of polymers to the inert surfaces to render them suitable for use as matrices. FIG. 6A exemplifies the grafting of a polymer to a tube containing an RF tag, linkage of scintillant to the surface, organic synthesis and then use of the resulting compound linked to the support in an assay. Thus, all steps are performed on the same platform. FIG. 6B also exemplifies a single platform protocol. FIG. 6C depicts the preparation of a tubular devices in which the matrix is the radiation grafted PTFE (polytetrafluoroethylene) and the memory is a transponder, such as the BMDS transponder or IDTAG™ transponder; FIG. 6D depicts a small chip (2 mm×2 mm×0.1 mm) encased in a radiation grafted polypropylene or PTFE ball (ball or bead or other such geometry) with a screw cap. It is understood herein that microreactors are not necessarily tubular in shape, but may be any geometry, and need not be hollow.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are, unless noted otherwise, incorporated by reference in their entirety. In the event a definition in this section is not consistent with definitions elsewhere, the definition set forth in this section will control.

As used herein, a bar code refers any array of optically readable marks of any desired size and shape that are arranged in a reference context or frame of, preferably, although not necessarily, one or more columns and one or more rows. For purposes herein, the bar code refers to any symbology, not necessary "bar" but may include dots, characters or any symbol or symbols.

As used herein, an optical memory refers to the symbology and the surface on which it is engraved or otherwise imprinted or refers to other optical devices. For purposes herein, an optical memory also includes optical recording media that may be appropriate for use in the recording devices and combinations herein and include, but are not limited to, optical discs, magneto-optical materials, photochromic materials, photoferroelectric materials, and photoconductive electro-optic materials. Optical memories also include memories, such as 2-D and 3-D optical memories that use optics, such as lasers, for writing and/or reading.

As used herein, an optical memory device (OMD) refers to a surface that is encoded with a code, preferably the 2-D bar code provided herein. For use herein, such devices include at least two surfaces, one of which is treated or formed from a matrix material treated to render it suitable for use as a support to which molecules or biological particles are linked, such as in chemical syntheses or as supports in assays, and the other that includes a code that can be optically read and then compared with information in a computer or other memory to interpret its meaning.

As used herein, symbology refers to the code, such as a bar code, that is engraved or imprinted on the OMD. The symbology is any code known or designed by the user. The symbols are associated with information stored in a remote computer or memory or other such device or means. For example, each OMD can be uniquely identified with an encoded symbology. The process steps or additions or manipulations to the associated molecules or biological particles can be recorded in a remote memory and associated with the code.

As used herein, machining as intended herein refers to a process that roughens the surface to alter the properties thereof, such as increasing porosity, whereby grafting is increased. The roughened surfaces typically feel rough to the touch. Such processes include, but are not limited to, using a lathe to render the surface ridged or make the surface rough, or forming a polymer by injection molding in a mold which has been rendered rough at the microscopic level by processes such as electric discharge machining and chemical etching.

As used herein, a rough surface refers to a surface that is produced by these processes. Such rough surfaces are generally rough to the touch and appear rough under a light microscope.

As used herein, loading refers to the number of reactive sites available for binding of macromolecules, small molecules or other substrates of interest on the grafted polymer or derivatized grafted polymer. Loading may be expressed, for example, as the number of amino groups (in $\mu$mol) per unit weight of the polymer (in mg) or per polymeric article (e.g., a tube).

As used herein, a matrix refers to any solid or semisolid or insoluble support on which a code is to which the memory device and/or the molecule of interest, typically a biological molecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrylamide non-covalent composite, polystyrene-polyacrylamide covalent composite, polystyrene-PEG (polyethyleneglycol) composite, silicon, rubber, and other materials used as supports for solid phase syntheses, affinity separations and purifications, hybridization reactions, immunoassays and other such applications. The matrix herein may be particulate or may be in the form of a continuous surface, such as a microtiter dish or well, a glass slide, a silicon chip with a surface adapted for linking of biological particles or molecules, a nitrocellulose sheet, nylon mesh, or other such materials. When particulate, typically the particles have at least one dimension in the 5–10 mm range or smaller. Such particles, referred collectively herein as "beads", are often, but not necessarily, spherical. Such reference, however, does not constrain the geometry of the matrix, which may be any shape, including random shapes, needles, fibers, elongated, etc. The "beads" may include additional components, such as magnetic or paramagnetic particles (see, e.g., Dyna beads (Dynal, Oslo, Norway)) for separation using magnets, fluorophores and other scintillants, as long as the additional components do not interfere with chemical reactions, data entry or retrieval from the memory.

Also contemplated herein, are the combination of "chips" or arrays that contain hundreds of thousands of probes (see, e.g., U.S. Pat. No. 5,525,531) linked to a matrix with a surface suitable for linking probes or other selected molecules or biological particles. Significantly, it is noted, however, that many surfaces, such as glass, require modification to render them suitable for use as supports. Any such surface must be treated to render it suitable for chemical syntheses or for adsorption of biological particles. Chemical syntheses require a support that not only has the proper surface characteristics (organic solvent wettability, chemical kinetics, etc.), but that also has a high density of functional groups. An untreated glass surface contains only a very small amount (less than 1 nmol/sq. mm) of hydroxy groups. It is also very hydrophilic and not very suitable for reactions in organic media. Therefore, the glass surface has to be modified to achieve high functional group density (~>10 nmol/mm$^2$) and proper hydrophobicity. Thus, as used herein, matrix refers to materials that have been so-treated. Therefore, a transponder in which the memory device is encased in a glass capsule for instance is not usable as is, but must be treated, either by coating at least one surface with a polymer, such as by grafting, derivatizing or otherwise activating the surface.

As used herein, scintillants include, 2,5-diphenyloxazole (PPO), anthracene, 2-(4'-tert-butylphenyl)-5-(4"-biphenyl)-1,3,4-oxadiazole (butyl-PBD); 1-phenyl-3-mesityl-2-pyrazoline (PMP), with or without frequency shifters, such as 1,4-bis(5-phenyl(oxazolyl)benzene) (POPOP); p-bis-o-methylstyrylbenzene (bis-MSB). Combinations of these fluors, such as PPO and POPOP or PPO and bis-MSB, in suitable solvents, such as benzyltoluene (see, e.g., U.S. Pat. No. 5,410,155), are referred to as scintillation cocktails.

As used herein a luminescent moiety refers to a scintillant or fluorophore used in scintillation proximity assays or in non-radioactive energy transfer assays, such as HTRF (homogeneous time-resolved fluorescence) assays.

As used herein, fluorescent resonance energy transfer (FRET) is an art-recognized term meaning that one fluorophore (the acceptor) can be promoted to an excited electronic state through quantum mechanical coupling with and receipt of energy from an electronically excited second fluorophore (the donor). This transfer of energy results in a decrease in visible fluorescence emission by the donor and an increase in fluorescent energy emission by the acceptor. Significant energy transfer can only occur when the donor and acceptor are sufficiently closely positioned since the efficiency of energy transfer is highly dependent upon the distance between donor and acceptor fluorophores.

As used herein, a fluoropolymer or fluoroelastomer refers to a compound composed of fluorinated monomeric units. For purposes herein, the surfaces of such materials are referred to collectively as fluoropolymeric surfaces.

The monomeric units contain one or more fluorine atoms and often are perfluorinated. In addition, fluoropolymers or fluoroelastomers may be copolymeric, wherein at least one of the monomer units forming the copolymer is fluorinated. Fluoropolymers, include, but are not limited to: as PTFE (polytetrafluoroethylene, TEFLON®), ETFE (ethylene-tetrafluoroethylene copolymer, TEFZEL®), ECTFE (ethylene chlorotrifluoroethylene, HALAR®), PCTFE (polychlorotrifluoroethylene), PVF (polyvinyl fluoride), PVDF (polyvinylidene fluoride, HYLAR®), FEP (polyperfluoroethylenelpropylene copolymer, FEP TEFLON®), PFA (tetrafluoroethylene-perfluoroalkyl-vinylether copolymer), HFP (hexafluoro-propylene), PPVE (perfluoropropyl vinyl ether) and many others, are highly inert to a wide variety of chemical transformations. Preferred fluoropolymers and fluoroelastomers include, but are not limited to: PTFE polytetrafluoro-ethylene, TEFLON®), ETFE (ethylene-tetrafluoroethylene opolymer, TEFZEL®), ECTFE (ethylene chlorotrifluoroethylene, HALAR®), PCTFE (polychlorotrifluoroethylene), PVF (polyvinyl fluoride), PVDF (polyvinylidene fluoride, HYLAR®), FEP (polyperfluoroethylene/propylene copolymer, FEP TEFLON®), PFA (tetrafluoroethylene-perfluoroalkyl-vinylether copolymer), HFP (hexafluoropropylene), PPVE (perfluoropropyl vinyl ether), poly(vinylidene fluoride-hexafluoropropylene) and poly(vinylidene fluoride-hexafluoropropylene-tetrafluoroethylene). Other such materials are also contemplated herein.

As used herein, a copolymer is a compound composed of two or more different monomeric units. Exemplary copolymers are ETFE (ethylene-tetrafluoroethylene copolymer, TEFZEL®), ECTFE (ethylene chlorotrifluoroethylene, HALAR®), FEP (polyperfluoroethylene/propylene copolymer, FEP TEFLON®) and PFA (tetrafluoroethylene-perfluoroalkyl-vinylether copolymer).

As used herein, matrix particles refer to matrix materials that are in the form of discrete particles. The particles have any shape and dimensions, but typically have at least one dimension that is 100 mm or less, preferably 50 mm or less, more preferably 10 mm or less, and typically have a size that is 100 mm$^3$ or less, preferably 50 mm$^3$ or less, more preferably 10 mm$^3$ or less, and most preferably 1 mm$^3$ or less. The matrices may also be continuous surfaces, such as microtiter plates (e.g., plates made from polystyrene or polycarbonate or derivatives thereof commercially available from Perkin Elmer Cetus and numerous other sources), and Covalink trays (Nunc), microtiter plate lids or a test tube, such as a 1 mL Eppendorf tube or smaller versions, such as 500 µL, 200 µL or smaller. Matrices that are in the form of containers refers to containers, such as test tubes and microplates and vials that are typically used for solid phase syntheses of combinatorial libraries or as pouches, vessels, bags, and microvessels for screening and diagnostic assays or as containers for samples, such as patient samples. Thus, a container used for chemical syntheses refers to a container that typically has a volume of about 1 liter, generally 100 mL, and more often 10 mL or less, 5 mL or less, preferably 1 mL or less, and as small as about 50 µL–500 µL, such as 100 µL or 250 µL or 200 µL. This also refers to multi-well plates, such as microtiter plates (96 well, 384 well, 1536 well or other higher density format). Such microplate will typically contain a memory device in, on, or otherwise in contact with in each of a plurality of wells.

As used herein, a matrix with a memory refers to a combination of a matrix with any means for storing information. Such memories include, a miniature recording device that stores multiple bits of data by which the matrix may be identified, preferably in a non-volatile memory that can be written to and read from by transmission of electromagnetic radiation from a remote host, such as a computer. By miniature is meant of a size less than about 10–20 mm$^3$ (or 10–20 mm in the largest dimension). Preferred memory devices or data storage units are miniature and are preferably smaller than 10–20 mm$^3$ (or 10–20 mm in its largest dimension) dimension, more preferably less than 5 mm$^3$, most preferably about 1 mm$^3$ or smaller. Alternatively, the memory may be fabricated as part of the matrix material or may be a chemical or biological-based memory means, such as those described herein, including the rhodopsin based memories and 3-D optical memories based on photochromic materials (see, e.g., U.S. Pat. Nos. 5,268,862, 5,130,362, 5,325,324; see, also, Dvornikov et al. (1996) Opt. Commun. 128:205–210; Dvornikov et al. (1996) Res. Chem. Intermed. 22:115–28; Dvornikov et al. (1994) Proc. SPIE-Int. Soc. Opt. Eng. 2297:447–51; Dvornikov et al. (1994) Mol. Cryst. Liq. Cryst. Sci. Technol., Sect. A 246:379–88; Dvornikov et al. (1994) J. Phys. Chem. 98:6746–52; Ford et al. (1993) Proc. SPIE-Int. Soc. Opt. 2026:604–613; Ford et al. Proc. SPIE-Int. Soc. Opt. Eng. 1853:5–13; Malkin et al. Res. Chem. Intermed. 19:159–89; Dvornikov et al. (1993) Proc. SPIE-Int. Soc. Opt. Eng. 1852:243–52; Dvornikov et al. (1992) Proc. SPIE-Int. Soc. Opt. Eng. 1662:197–204; Prasad et al. (1996) Mater. Res. Soc. Symp. Proc. 413:203–213). Alternatively, the memory may be an optical bar code, such as the 2-D optical bar codes described herein. Thus, the term memory with matrix refers generically to any combination (association) between a matrix and any means for storing information.

As used herein, a microreactor refers to combinations of matrices with memories with associated, such as linked or proximate, biological particles or molecules. It is produced, for example, when the molecule is linked thereto or synthesized thereon. It is then used in subsequent protocols, such as immunoassays and scintillation proximity assays.

As used herein, a memory is a data storage unit (or medium) with programmable memory, preferably a non-volatile memory; or alternatively is a symbology on a surface, such as a bar code, whose identity and as for which associate information is stored in a remote memory, such as a computer memory.

As used herein, programming refers to the process by which data or information is entered and stored in a memory. A memory that is programmed is a memory that contains retrievable information.

As used herein, remotely programmable, means that the memory can be programmed (read from and written to) without direct physical or electrical contact or can be programmed from a distance, typically at least about 10 mm, although shorter distances may also be used, such as instances in which the information comes from surface or proximal reactions or from an adjacent memory or in instances, such as embodiments in which the memories are very close to each other, as in microtiter plate wells or in an array.

As used herein, a recording device (or memory device) is an apparatus that includes the data storage unit with programmable memory, and, if necessary, means for receiving information and for transmitting information that has been recorded. It includes any means needed or used for writing to and reading from the memory. The recording devices intended for use herein, are miniature devices that preferably are smaller than 10–20 mm$^3$ (or 10–20 mm in their largest dimension), and more preferably are closer in size to 1 mm$^3$ or smaller that contain at least one such memory and means for receiving and transmitting data to and from the memory. The data storage device also includes optical memories and bar codes, on devices such as OMDs.

As used herein, a data storage unit with programmable memory includes any data storage means having the ability to record multiple discrete bits of data, which discrete bits of data may be individually accessed (read) after one or more recording operations. Thus, a matrix with memory is a combination of a matrix material with a data storage unit.

As used herein, programmable means capable of storing unique data points. Addressable means having unique locations that may be selected for storing the unique data points.

As used herein, a host computer or decoder/encoder instrument is an instrument that has been programmed with or includes information (i.e., a key) specifying the code used to encode or decode the memory devices. This instrument or one linked thereto transmits the information and signals to the recording device and it, or another instrument, receives the information transmitted from the recording device upon receipt of the appropriate signal. This instrument thus creates the appropriate signal to transmit to the recording device and can interpret transmitted signals. For example, if a "1" is stored at position 1,1 in the memory of the recording device means, upon receipt of this information, this instrument or computer can determine that this means the linked molecule is, for example, a peptide containing alanine at the N-terminus, an organic group, organic molecule, oligonucleotide, or whatever this information has been pre-determined to mean. Alternatively, the information sent to and transmitted from the recording device can be encoded into the appropriate form by a person.

As used herein, an identification station refers to a device that reads memories and includes any such components and software necessary to effect such reading and communication of information to the user or to other devices, such as a host computer. Exemplary stations are known (see, e.g., International Patent Application Publication No. WO 97/12680).

As used herein, an electromagnetic tag or electronic tag is a recording device that has a memory that contains unique data points that correspond to information that identifies molecules or biological particles linked to, directly or indirectly, in physical contact with or in proximity (or associated with) to the device. Thus, electromagnetic tagging is the process by which identifying or tracking information is transmitted (by any means and to any recording device memory, including optical and magnetic storage media) to the recording device.

As used herein, proximity means within a very short distance, generally less than 0.5 inch, typically less than 0.2 inches. In particular, stating that the matrix material and memory, or the biological particle or molecule and matrix with memory are in proximity means that, they are at least or at least were in the same reaction vessel or, if the memory is removed from the reaction vessel, the identity of the vessel containing the molecules or biological particles with which the memory was proximate or linked is tracked or otherwise known.

As used herein, associated with means that the memory must remain in proximity to the molecule or biological particle or must in some manner be traceable to the molecule or biological particle. For example, if a molecule is cleaved from the support with memory, the memory must in some manner be identified as having been linked to the cleaved molecule. Thus, a molecule or biological particle that had been linked to or in proximity to a matrix with memory is associated with the matrix or memory if it can be identified by querying the memory.

As used herein, high current is from about 8–12 amps.

As used herein, antifuse refers to an electrical device that is initially an open circuit that becomes a closed circuit during programming, thereby providing for non-volatile memory means and, when accompanied by appropriate transceiver and rectification circuitry, permitting remote programming and, hence identification. In practice, an antifuse is a substantially nonconductive structure that is capable of becoming substantially conductive upon application of a predetermined voltage, which exceeds a threshold voltage. An antifuse memory does not require a constant voltage source for refreshing the memory and, therefore, may be incorporated in a passive device. Other memories that may be used include, but are not limited to: EEPROMS, DRAMS and flash memories.

As used herein, flash memory is memory that retains information when power is removed (see, e.g., U.S. Pat. Nos. 5,452,311, U.S. Pat. No. 5,452,251 and U.S. Pat. No. 5,449,941). Flash memory can be rewritten by electrically and collectively erasing the stored data, and then by programming.

As used herein, passive device refers to an electrical device which does not have its own voltage source and relies upon a transmitted signal to provide voltage for operation.

As used herein, electromagnetic (EM) radiation refers to radiation understood by skilled artisans to be EM radiation and includes, but is not limited to radio frequency (RF; low kilohertz (80 KHz) up to about 800 MHz–1 GHz), infrared (IR), visible, ultraviolet (UV), radiation, microwave (i.e., 800 MegaHz–300 GHz (corresponding to wavelengths of 1 meter to 1 mm), preferably just beyond the RF range), sonic waves, X-rays, and laser light.

As used herein, information identifying or tracking a biological particle or molecule, refers to any information that identifies the molecule or biological particle, such as, but not limited to the identity particle (i.e. its chemical formula or name), its sequence, its type, its class, its purity, its properties, such as its binding affinity for a particular ligand. Tracking means the ability to follow a molecule or biological particle through synthesis and/or process steps. The memory devices herein store unique indicators that represent any of this information.

As used herein, combinatorial chemistry is a synthetic strategy that produces diverse, usually large, chemical libraries. It is the systematic and repetitive, covalent connection of a set, the basis set, of different monomeric building blocks of varying structure to each other to produce an array of diverse molecules (see, e.g., Gallop et al. (1994) *J. Medicinal Chemistry* 37:1233–1251). It also encompasses other chemical modifications, such as cyclizations, eliminations, cleavages, etc., that are carried in manner that generates permutations and thereby collections of diverse molecules.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials.

As used herein, a molecule refers to any molecule, particularly a macromolecule or constituent thereof, that is linked to the solid support. Typically such molecules are compounds or components or precursors thereof, such as peptides, amino acids, small organics, oligonucleotides or monomeric units thereof. A monomeric unit refers to one of the constituents from which the resulting compound is built. Thus, monomeric units include, nucleotides, amino acids, and pharmacophores from which small organic molecules are synthesized.

As used herein, the molecules in the combinations include any molecule, including nucleic acids, amino acids, other biopolymers, and other organic molecules, including peptidomimetics and monomers or polymers of small organic molecular constituents of non-peptidic libraries, that may be identified by the methods here and/or synthesized on matrices with memories as described herein.

As used herein, the term "bio-oligomer" refers to a biopolymer of less than about 100 subunits. A bio-oligomer includes, but is not limited to, a peptide, i.e., containing amino acid subunits, an oligonucleotide, i.e., containing nucleoside subunits, a peptide-oligonucleotide chimera, peptidomimetic, and a polysaccharide.

As used herein, the term "sequences of random monomer subunits" refers to polymers or oligomers containing sequences of monomers in which any monomer subunit may precede or follow any other monomer subunit.

As used herein, the term "library" refers to a collection of substantially random compounds or biological particles expressing random peptides or proteins or to a collection of diverse compounds. Of particular interest are bio-oligomers, biopolymers, or diverse organic compounds or a set of compounds prepared from monomers based on a selected pharmacophore.

As used herein, an analyte is any substance that is analyzed or assayed in the reaction of interest. Thus, analytes include the substrates, products and intermediates in the reaction, as well as the enzymes and cofactors.

As used herein, multianalyte analysis is the ability to measure many analytes in a single specimen or to perform multiple tests from a single specimen. The methods and combinations herein provide means to identify or track individual analytes from among a mixture of such analytes.

As used herein, a fluorophore or a fluor is a molecule that readily fluoresces; it is a molecule that emits light following interaction with radiation. The process of fluorescence refers to emission of a photon by a molecule in an excited singlet state. For scintillation assays, combinations of fluors are typically used. A primary fluor that emits light following interaction with radiation and a secondary fluor that shifts the wavelength emitted by the primary fluor to a higher more efficiently detected wavelength.

As used herein, complete coupling means that the coupling reaction is driven substantially to completion despite or regardless of the differences in the coupling rates of individual components of the reaction, such as amino acids. In addition, the amino acids, or whatever is being coupled, are coupled to substantially all available coupling sites on the solid phase support so that each solid phase support will contain essentially only one species of peptide.

As used herein, the biological activity or bioactivity of a particular compound includes any activity induced, potentiated or influenced by the compound in vivo or in vitro. It also includes the abilities, such as the ability of certain molecules to bind to particular receptors and to induce (or modulate) a functional response. It may be assessed by in vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified. Pharmaceutically-acceptable salts include, but are not limited to, salts of alkali metals and alkaline earth metals, including but not limited to sodium salts, potassium salts, lithium salts, calcium salts and magnesium salts; transition metal salts, such as zinc salts, copper salts and aluminum salts; polycationic counter ion salts, such as but not limited ammonium and substituted ammonium salts and organic amine salts, such as hydroxyalkylamines and alkylamines; salts of mineral acids, such as but not limited to hydrochlorides and sulfates, salts of organic acids, such as but not limited acetates, lactates, malates, tartrates, citrates, ascorbates, succinates, butyrate, valerate and fumarates.

As used herein, substantially pure means sufficiently homogeneous to appear free of readily detectable impurities as determined by standard methods of analysis, such as thin layer chromatography (TLC), mass spectrometry (MS), size exclusion chromatography, gel electrophoresis, particularly agarose and polyacrylamide gel electrophoresis (PAGE) and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a receptor refers to a molecule that has an affinity for a given ligand. Receptors may be naturally-occurring or synthetic molecules. Receptors may also be referred to in the art as anti-ligands. As used herein, the terms, receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles.

Examples of receptors and applications using such receptors, include but are not restricted to:
  a) enzymes: specific transport proteins or enzymes essential to survival of microorganisms, which could serve as targets for antibiotic (ligand) selection;
  b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases;
  c) nucleic acids: identification of ligand, such as protein or RNA, binding sites;
  d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant (see, e.g., U.S. Pat. No. 5,215,899);
  e) hormone receptors: determination of the ligands that bind with high affinity to a receptor is useful in the development of hormone replacement therapies; for example, identification of ligands that bind to such receptors may lead to the development of drugs to control blood pressure; and
  f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, an epitope refers to a portion of an antigen molecule that is delineated by the area of interaction with the subclass of receptors known as antibodies.

As used herein, a ligand is a molecule that is specifically recognized by a particular receptor. Examples of ligands, include, but are not limited to, agonists and antagonists for cell membrane receptors, toxins and venoms, viral epitopes, hormones (e.g., steroids), hormone receptors, opiates, peptides, enzymes, enzyme substrates, cofactors, drugs, lectins, sugars, oligonucleotides, nucleic acids, oligosaccharides, proteins, and monoclonal antibodies.

As used herein, multiplexing refers to performing a series of synthetic and processing steps and/or assaying steps on the same platform (i.e. solid support or matrix) or coupled together as part of the same automated coupled protocol, including one or more of the following, synthesis, preferably accompanied by writing to the linked memories to identify linked compounds, screening, including using protocols with matrices with memories, and compound identification by querying the memories of matrices associated with the selected compounds. Thus, the platform refers system in which all manipulations are performed. In general it means that several protocols are coupled and performed sequentially or simultaneously.

As used herein, a platform refers to the instrumentation or devices in which on which a reaction or series of reactions is(are) performed.

As used herein a protecting group refers to a material that is chemically bound to a monomer unit that may be removed upon selective exposure to an activator such as electromagnetic radiation and, especially ultraviolet and visible light, or that may be selectively cleaved. Examples of protecting groups include, but are not limited to: those containing nitropiperonyl, pyrenylmethoxy-carbonyl, nitroveratryl, nitrobenzyl, dimethyl dimethoxybenzyl, 5-bromo-7-nitroindolinyl, o-hydroxy-alpha-methyl cinnamoyl, and 2-oxymethylene anthraquinone.

Also protected amino acids are readily available to those of skill in this art. For example, Fmoc and Boc protected amino acids can be obtained from Fluka, Bachem, Advanced Chemtech, Sigma, Cambridge Research Biochemical, Bachem, or Peninsula Labs or other chemical companies familiar to those who practice this art.

As used herein, the abbreviations for amino acids and protective groups are in accord with their common usage and the IUPAC-IUB Commission on Biochemical Nomenclature (see, (1972) *Biochem.* 11: 942–944). Each naturally occurring L-amino acid is identified by the standard three letter code or the standard three letter code with or without the prefix "L-"; the prefix "D-" indicates that the stereoisomeric form of the amino acid is D. For example, as used herein, Fmoc is 9-fluorenylmethoxycarbonyl; BOP is benzotriazol-1-yloxytris(dimethylamino) phosphonium hexafluorophosphate, DCC is N,N'-dicyclohexylcarbodiimide; DDZ is dimethoxydimethylbenzyloxycarbonyl; DMT is dimethoxytrityl; HBTU is 2-(1H-benzotriazol-1-yl)- 1,1,3,3-tetramethyluronium hexafluorophosphate; NV is nitroveratryl; NVOC is 6-nitroveratryloxycarbonyl; TFA is trifluoroacetic acid; DMF is N,N-dimethylformamide; Boc is tert-butoxycarbonyl; ACN is acetonitrile; HF is hydrogen fluoride; HFIP is hexafluoroisopropanol; HPLC is high performance liquid chromatography; FAB-MS is fast atom bombardment mass spectrometry; DCM is dichloromethane, Bom is benzyloxymethyl; Pd/C is palladium catalyst on activated charcoal; DIC is diisopropylcarbodiimide; [For] is formyl; PyBop is benzotriazol-1-yl-oxy-trispyrrolidinophosphonium hexafluorophosphate; POPOP is 1,4,-bis(5-phenyl(oxazolyl)benzene); PPO is 2,5-diphenyloxazole; butyl-PBD is 2-(4'-tert-butylphenyl)-5-(4"-biphenyl)- 1,3,4-oxadiazole; PMP is (1-phenyl-3-mesityl-2-pyrazoline); DIEA is diisopropylethylamine; NMP is N-methylpyrrolidone; PAL is pyridylalanine; HATU is O(7-azabenzotriaol-1-yl)-1,1,3,3-tetramethyluronium hexafluorophosphate; THF is tetrahydrofuran; and EDT is 1,2-ethanedithiol.

A. Grafting and Grafted Composite Polymeric Materials

Fluoropolymers (and fluoroelastomers), as well as other polymeric materials, have been rendered suitable for derivatization by grafting another polymer onto the surface by a process known as irradiation induced graft polymerization. Such grafting is usually promoted by irradiating the fluoropolymer with radiation such as y-rays, X-rays, electron beams, plasma discharge, corona discharge, glow discharge plasma or radiation provided by a $^{60}$Co source. The irradiation may be performed in the presence of a monomer (or monomers) forming the graft polymer, such as styrene, acrylic acid, methylacrylic acid, 2-hydroxymethylacrylate and other such monomers, or the monomer (or monomers) may be added after irradiation. See, generally, U.S. Pat. Nos. 4,506,035, 4,602,045, 4,954,256, 5,229,172, 5,232,600, 5,376,400, 5,576,106 and 5,587,208. The process may also be carried out in the presence of oxygen or ceric ion as promoters of the polymerization. Irradiation induced graft polymerization is also useful for producing polymeric grafts on polymers other than fluoropolymers, such as PP (polypropylene) and PE (polyethylene). Another method for graft polymerization onto fluoropolymers involves reductive activation of the fluoropolymer (see, U.S. Pat. No. 4,661,383). In this method, the fluoropolymer is reduced with, e.g., an alkali metal benzoin dianion to provide a thin layer of polyacetylene on the surface of the fluoropolymer. Subsequent doping with, e.g., potassium naphthalide, followed by grafting of a copolymer provides the desired grafted composites.

The composite fluoropolymeric materials that result from application of the above processes typically have insufficient grafted polymer thereon for solid phase syntheses and screening.

1. Methods for Increasing Grafting

Methods are provided herein for enhancing radiation grafting of polymers on fluoropolymers and fluoroelastomers. The methods provided herein may be used in conjunction with any known method, such as those described above and elsewhere herein, will enhance the grafting, thereby resulting is composite materials that are suitable for use as solid supports for syntheses and screening. The methods herein are intended for use for grafting any polymeric surface, particularly a fluoropolymer, for any application that requires high loading.

To effect grafting the polymer tubes are irradiated under a $^{60}$Co source. The dose rate can be empirically determined. Rates of $0.01 \times 10^6$ to $1 \times 10^6$ rads (r)/h are typical and the most effective rate was $0.1 \times 10^6$ r/h. A total dose of 0.5–10× $10^6$ rads was typical and the most effective dose was 2.6–2.9×$10^6$ rads. In a preferred embodiment, the method involves inclusion of an acid, preferably a mineral acid, in the grafting reaction. The use of the acid increases the amount of grafting compared to grafting in the absence of the acid. An exemplary protocol, particularly useful for increasing level of grafting on fluoropolymers, which heretofore had not been achieved, is provided in the Examples.

Preferred acids for use in the method are mineral acids, more preferably sulfuric acid and nitric acid. Acid concentrations are generally about 0.01–1 M, preferably about 0.025–0.5 M, more preferably 0.05–0.2 M. Increases in the level of grafting in the grafted polymer were observed from about 10 to about 300%, generally on the order of about 30–300%, and often 50–200%. In all embodiments, radiation grafting is preferably performed under oxygen-free conditions at ambient temperature. The level of grafting should not be so high as to compromise the mechanical integrity of the resulting grafted polymer. The resulting grafted fluoropolymer composites have greater than 5%, typically greater than 10% and preferably greater than 20% by weight of grafted polymer.

In a most preferred embodiment, radiation grafting of styrene on to ETFE (TEFZEL®) is performed in the presence of 0.1 M sulfuric acid. The styrene concentration is about 25–50%, preferably 45%, in methanol solution. In this embodiment, the amount of polystyrene grafted onto the ETFE is at least about 50% higher than grafting in the absence of acid. Under preferred conditions, the grafting was about 300% higher than in the absence of acid.

In another preferred embodiment, the method involves machining of the polymer onto which the graft is to be added, preferably a fluoropolymer, prior to grafting. Such machining increases the level of grafting on the polymer. Machining is preferably performed with a lathe, but may also be performed using any method known to those of skill in the art which will produce a rough surface. The Table 1 provides exemplary conditions for machining.

TABLE 1

| machine set-up | Spindle speed RPM | Feed rate FPR[a] |
| --- | --- | --- |
| PTFE | 5,000 | 0.0025 |
| ETFE | 2,200 | 0.0045 |

[a]FPR = feet per revolution

In another preferred embodiment, the method involves the generation of a rough surface on the polymer onto which the graft is to be added, preferably a fluoropolymer, by either the process of electric discharge machining (EDM) or the process of chemical etching of the cavity mold for the polymer. EDM is normally performed using a moderate current, for example, 7.25 amps, with a 50/50 on/off pulse to create a cavity with well defined detail and shape. In the instant embodiment, EDM is performed at a high current, for example, 8–12 amps, preferably 10 amps, with an on/off pulse of, e.g., 1500–2500, preferably 2000, $\mu$sec on/7–11, preferably 9 $\mu$sec off to provide a rough surface on the mold cavity. Additionally, the mold design allows for unusually high injection pressures, e., 10000–15000 pounds per square inch (psi), preferably 15000 psi, so that the resulting polymeric surface is also rough. Preferred conditions are: high current from about 8–12 amps, and an on/off pulse rate of about 1 500–2500 $\mu$sec on/about 7–11 $\mu$sec off; and where injection molding is performed at an injection pressure of at least about 10000 pounds per square inch.

Alternatively, the cavity mold may be chemically etched using methods known to those of skill in the art. For example, a mineral acid such as hydrochloric acid may be used to etch a steel mold. Chemical etching may also be performed by commercial sources, for example, by Mold-Tech, a Division of Roehien Industries (a Standex company), Walnut, Calif. Table 2 provides exemplary amine loading onto ETFE molded after from EDM and chemical etching of the mold cavity. As can be seen from the data in Table 2, ETFE formed from EDM-etched molds generally provides higher amine loading than ETFE from chemically-etched molds.

TABLE 2

| Sample # | 1 | 2 | 3 | 4 | 5 | 6 | 7 | 8 | 9 | 10 | 11 |
| --- | --- | --- | --- | --- | --- | --- | --- | --- | --- | --- | --- |
| method | EDM | EDM | EDM | EDM | etch | etch | etch | etch | etch | etch | etch |
| Surface area mm$^2$ | 144 | 144 | 144 | 144 | 144 | 144 | 144 | 144 | 144 | 144 | 144 |
| NH$_2$ $\mu$mol | 12 | 9 | 10 | 14 | 10 | 10 | 9 | 9 | 9 | 9 | 9 |

In a more preferred embodiment, the amount grafted is increased by using polymer onto which the graft is to be added that has a roughened surface, and also including an acid, preferably a mineral acid, during the grafting reaction. The polymer with a rough surface may be prepared by the methods described herein or by other methods known to those of skill in the art.

Functional groups are introduced by selection of the monomers, such as styrene, choloromethylstyrene, methylacrylate, 2-hydroxymethyl-acrylate and/or other vinyl monomers containing one or more functional groups. Alternatively, the grafted copolymer may be derivatized with a functional group, including, but not limited to, alcohols, amines, alkyl halides, phenols, aldehydes, nitrites, carboxyl groups and the like, suitable for combinatorial synthesis or assays. For example, aminomethyl functional groups may be introduced by first radiation grafting polystyrene onto the surface of tubes or other geometry devices fabricated from any of the above-noted polymers, followed by functionalization using N-(hydroxymethyl)phthalimide with trifluoromethanesulfonic acid as a catalyst. The polystyrene grafted polymer tube is thoroughly washed before use to remove residual monomer, non-attached polystyrene and additives remaining from the radiation grafting. The amidoalkylation proceeds smoothly at room temperature in 50% (v/v) trifluoroacetic acid-dichloromethane solvent for 24 hours. Loading can be controlled by changing the concentrations of reagent, catalyst and/or reaction time. Hydrazinolysis in refluxing ethanol gives the aminomethyl polystyrene grafted polymer tube. Adjustable loading range is on the order of 0.5–100 $\mu$mol per tube, depending the size of the tube and the polymer.

A carboxylic acid group was introduced by using acrylic acid or functionalization of grafted polystyrene. The polystyrene grafted tube was functionalized using n-butyllithium and N,N N',N'-tetramethylethylen-diamine in hexane at 60° C., after which the lithiated polymer tube was exposed to $CO_2$. The carboxylic acid loading was about 1–20 $\mu$mol per tube. Detailed protocols are set forth in the EXAMPLES.

It also has been found that dilution of styrene with an alcohol, preferably methanol, ethanol or isopropanol, more preferably methanol, enhances the rate of grafting, particularly in an embodiment where the tubes are made from PTFE. Dilutions, which can be determined empirically for each material, from 5% to 70% have been tested. PTFE and PE tubes have the highest styrene grafting at a 50% dilution in methanol, and polypropylene tubes have the best performance when grafted at a 35% dilution in methanol.

2. Composites

Provided herein are the resulting solid composite polymeric materials, particularly fluoropolymeric materials, such as, but not limited to polytetrafluoroethylene (PTFE, TEFLON®), ethylene-tetrafluoroethylene copolymer (ETFE; such as that sold under the trade mark TEFZEL by DuPont), poly(chlorotrifluoroethylene) resin (PCTFE), tetrafluoroethylene-perfluoroalkyl-vinylether copolymer (PFA), ethylene-chlorotrifluoroethylene copolymer (ECTFE, HALAR®), HFP (hexafluoropropylene), PPVE (perfluoropropyl vinyl ether), polyvinyl fluoride (PVF), polyvinylidene fluoride (PVDF, HYLAR®) and tetrafluoroethylene-hexafluoropropylene copolymer (FEP TEFLON®), coated or grafted with suitable materials, including, but not limited to, polymers composed of styrene, choloromethylstyrene, methylacrylate, 2-hydroxymethylacrylate and/or other vinyl monomers containing one or more functional groups.

The resulting grafted materials can be formed into a desired shape, further derivatized where necessary, and used as a solid support for any desired purpose, but particularly methods disclosed herein, including organic syntheses and assays, or other applications known to those of skill in the art that require solid supports. Fluorophores, scintillants and other such compounds may also be incorporated into the surface or linked thereto.

These grafted materials, which may be formed into tubes or other geometries or made into particles, in preferred embodiments here, encased or are embedded with or otherwise combined, either permanently or removably, with a memory, such as an RF tag, or imprinted or engraved with a symbology. The resulting devices are herein referred to as microreactors. For example, the diameter or dimensions of the tube or other geometry device can be any desired size, with 0.1 mm to 20 mm presently preferred and 2 mm to 5 mm more preferred.

The surface of the matrix material that is treated or adapted for linking biological particles or molecules may include linkers for effecting the linking. In certain embodiments, a variety of linkers with differential cleavage properties may be used, thereby providing a means to selectively cleave linked molecules after synthesis and/or screening, or linked biological particles before or after screening.

1. Matrices with Memories

The radiation grafted materials, particularly the fluoropolymers, are particularly intended for use as matrix supports for any application for which such supports are used. Preferred uses include the use as the support matrix in a matrix with memory (see, e.g., International PCT application Nos. WO 97/12680 and WO 96/36436), such as the MICROKAN™ and MICROTUBE™ microreactors or other such microreactors. The improvements herein involve using grafted materials prepared by the methods herein as the surface of the MICROTUBE™ microreactor are as the particulates in the MICROKAN™ microreactors.

For purposes herein, matrices refer to supports used to retain molecules and biological particles, such as for chemical synthesis and to solid continuous surfaces in which the surface is used as the support, and containers, such as microplates and test tubes. Matrices used for supports will be derivatized or otherwise suitable for retaining molecules or biological particles.

Matrices, which are generally insoluble materials used to immobilize ligands and other molecules, have application in many chemical syntheses and separations. Matrices are used in affinity chromatography, in the immobilization of biologically active materials, and during chemical syntheses of biomolecules, including proteins, amino acids and other organic molecules and polymers. The preparation and use of matrices is well known to those of skill in this art; there are many such materials and preparations thereof known.

The matrices contemplated herein are the relatively inert polymers that are suitably grafted by ionizing radiation (see, e.g., FIG. 5, which depicts a particular embodiment) as described herein to permit attachment of a coating of polystyrene or other such polymer that can be derivatized and used as a support. Recording devices, such as electronic tags (microtags or microchips) that are often coated with a plastic or other insert material, can be treated with ionizing radiation so that selected monomers can be grafted to render the surface suitable for chemical syntheses using the methods herein.

The memory can be part of a recording device containing a data storage unit(s) containing the memory, which is preferably remotely readable and may also be remotely addressable. The recording device, includes, in addition to the memory, means for receiving information for storage in the memory and/or for retrieving information stored in the memory. Such means is typically an antenna, which also serves to provide power in a passive device when combined with a rectifier circuit to convert received energy, such as RF, into voltage, that can be tuned to a desired electromagnetic frequency to program the memory. Power for operation of the recording device may also be provided by a battery attached directly to the recording device, to create an active device, or by other power sources, including light and chemical reactions, including biological reactions, that generate energy.

Preferred frequencies are any that do not substantially alter the molecular and biological interactions of interest, such as those that are not substantially absorbed by the molecules or biological particles linked to the matrix or in proximity of the matrix, and that do not alter the support properties of the matrix. Radio frequencies are presently preferred, but other frequencies, such as microwave or the higher end of the radiofrequency range (300 MHz 800 MHz) that approaches the microwave range are also preferred. Other frequencies include radar and infrared. Optical lasers may be used, as long as the selected frequency or optical laser does not interfere with the interactions of the molecules or biological particles of interest. Thus, information in the form of data points corresponding to such information is stored in and retrieved from the data storage device by application of a selected electromagnetic radiation frequency, which preferably is selected to avoid interference from any background electromagnetic radiation.

A preferred recording device for use in the combinations herein is a single substrate of a size preferably less than about 10 to 20 mm$^3$ (or 10–20 mm in its largest dimension, most preferably 2 mm or less), that includes a remotely programmable data storage unit(s) (memory), preferably a non-volatile memory, and an antenna for receiving or transmitting an electromagnetic signal (and in some embodiments for supplying power in passive devices when combined with a rectifier circuit) preferably a radio frequency signal; the antenna, rectifier circuit, memory and other components are preferably integrated onto a single substrate, thereby minimizing the size of the device. An active device, i.e., one that does not rely on external sources for providing voltage for operation of the memory, may include a battery for power, with the battery attached to the substrate, preferably on the surface of the substrate. Vias through the substrate can then provide conduction paths from the battery to the circuitry on the substrate. The device is rapidly or substantially instantaneously programmable, preferably in less than 5 seconds, more preferably in about 1 second, and more preferably in about 50 to 100 milliseconds or less, and most preferably in about 1 millisecond or less. In a passive device that relies upon external transmissions to generate sufficient voltage to operate, write to and read from an electronic recording device, the preferred memory is non-volatile, and may be permanent. Such memories may rely antifuse-based architecture or flash memory. Other memories, such as electrically programmable erasable read only memories (EEPROMs) based upon other architectures also can be used in passive devices. In active recording devices that have batteries to assure continuous power availability, a broader range of memory devices may be used in addition to those identified above. These memory devices include dynamic random access memories (DRAMS, which refer to semiconductor volatile memory devices that allow random input/output of stored information; see, e.g., U.S. Pat. Nos. 5,453,633, 5,451,896, 5,442,584, 5,442,212 and 5,440,511), that permit higher density memories, and EEPROMs.

Monolithic devices [see, e.g., International PCT application Ser. No. 97/12680; see, also, U.S. Pat. No. 4,857,893] are among the preferred electromagnetically programmable memories. The monolithic devices are designed to be addressable and programmable in the microwave range or in the higher radiofrequency range. Thus, devices that are programmable in the gigahertz and microwave range are among the preferred devices.

Of interest herein, are devices that are prepared by inserting the recording device into a "tube" (see, e.g., FIG. 5) formed from the radiation grafted material prepared as described herein. Preferably prior to introducing (and preferably sealing) the recording device inside, the tube or encasing material is treated with ionizing radiation to render the surface suitable for grafting selected monomers, such as styrene (see, e.g., Maeji et al. (1994) *Reactive Polymers* 22:203–212; Ang et al. in Chapter 10: Application of Radiation Grafting in Reagent Insolubilization, pp 223–247; and Berg et al. (1989) *J. Am. Chem. Soc.* 111:8024–8026) as described herein.

These hollow devices (of any desired shape or geometry), referred to herein as microreactors, may contain a recording device and/or may include a code engraved, such as by a laser, or otherwise imprinted on the surface or combinations thereof. The tubular device may be sealed or open and retain the recording device by friction or by virtue of crimps in the surface. The tubular devices are preferably made of a fluoropolymer, such as TEFLON® (polytetrafluoroethylene (PTFE)), polyethylene, high density polyethylene, polypropylene, polystyrene, polyester, ceramic, composites of any of these materials and other such materials and grafted with monomers using the methods provided herein.

These devices are typically of a size used in immunoassays or hybridization reactions, generally a liter or less, typically less than 100 mL, and often less than about 10 mL in volume, typically 100 μL–500 μL, particularly 200–250 μL.

Other devices of interest, are polymeric supports, particularly fluoropolymer or polypropylene supports, generally about 5–10 mm in the largest dimension, and preferably a cube or other such shape, that are marked with a code, and tracked using a remote memory. These microvessels can be marked with a code, such as a bar code, alphanumeric code, the 2-D optical bar code provided herein, or other mark or include an optical memory, for identification, particularly in embodiments in which the memory is not in proximity to the matrix, but is remote therefrom and used to store information regarding each coded vessel.

The microreactors, such as those in which the recording device(s) is(are) introduced inside the material or where material is encases around the device and the resulting matrix with memory "tubes" (microreactors, see, e.g., FIG. 5), are used for chemical synthesis or linkage of selected molecules or biological particles. These "tubes" are preferably synthesized from an inert resin, such as a polypropylene (e.g., a Moplen resin, V29G PP resin from Montell, Newark Del., a distributor for Himont, Italy) or fluoropolymeric resin, which resins are grafted as described herein. Any inert matrix that can then be functionalized or to which derivatizable monomers can be grafted by the method provided herein is suitable.

Preferably herein, the fluoropolymeric material is formed into tubes or other suitable shapes, then grafted and then the recording device inserted inside or the symbology imprinted or engraved therein. These tubular or other shaped microreactors with grafted monomers are then used as supports for synthesis, and/or for assays or for multiplexed processes, including synthesis and assays or other multistep procedures. Although denoted a "tube", the device may be any shape formed from a continuous surface fabricated from an inert polymer, enclosing a hollow space comprising about 5 mL or less and including at least one orifice. Thus, the microreactor body is preferably hollow with an interior volume of less than about 5 mL, typically less than 1 or 2 mL; and the inert polymer is inert with respect to solvents and reagents used for protein synthesis, oligonucleotide synthesis, or organic synthesis or any assays for biological or pharmacological activity.

Such tubes may also have snap on or screw lids or caps so that, in embodiments in which the memory device is, for example, a chip, the memory device or chip is removable. For example, they may be conical tubes like Eppendorf tubes, with a snap on top, preferably a flat top. The tubes will be of a size to accommodate a memory device and thus may be as small as about 2 mm×2 mm×0.1 mm to hold the small 2 mm×2 mm×0.1 mm device described herein. They will be fabricated from polypropylene, a fluoropolymer or other suitable material and radiation grafted, see above, and Examples, below, preferably prior to introduction of the memory device.

The "tubes" may have no lids and instead retain any memory device by virtue of friction. Hollow and open "tubes" are presently preferred. They may have a nonuniform coating on the surface so that differential loading may be achieved or so different portions are suitable for different assays. They may be designed to be readily chopped or cut into pieces so the portion with a memory serves to store the linked molecules or biological particles as bits or pieces of the device are introduced into various assays or used for other purposes. These alternative shapes are, however, exemplary and are not intended to be limiting.

In a preferred embodiment microreactors, such as those described above, typically has about a 2–15, preferably about 7, millimeter outer diameter, and is manufactured from a polypropylene material, or a fluoropolymeric material, including but not limited to, PTFE or ETFE (TEFZEL®), or any other suitable material. Additionally, each of these microreactors has synthesis resin grafted onto its inner and/or outer surfaces using the methods provided herein.

The microreactors can be formed by extruding the material from an extrusion mold and allowing the material to cool. Typically, an extrusion process includes melting the material to be extruded and forcing the molten material through a mold. Various interior characteristics of the microreactors can be formed by inserting a mandrel within the center portion of the mold such that when the material is forced through the mold, the mold forms the outside surface of the microreactor, and the mandrel forms the inside surface of the microreactor.

Alternatively, extrusion may involve a continuous process whereby the molten polymer is forced through a nozzle and the resulting material is then cut to the desired dimensions. Molding a polymer involves extruding the polymer into a shape, letting the polymer cool and harden, then opening the mold and removing the part. This type of molding would be a batch process. Molding and extrusion of materials is well known in the art, and only described generally herein for reference. The surfaces are treated grafted as described herein. The memories are preferably then added.

For example, areas within each microreactor are sized to receive a transponder chip, i.e. a microtag, which can be forcibly inserted, or swaged, into the center portion of the microreactor. In order to retain the microtag within the microreactor, the portions of the tube which contact the microtag should be at least slightly pliable to provide the necessary contact force. With these devices, syntheses are performed on the surface. Instead of or in addition to, the solid tube can be engraved or imprinted with a symbology or include an optical memory or other tag, or combinations thereof. For example, the two-dimensional bar codes may be imprinted, engraved or otherwise included on the devices.

In alternative embodiments, microreactor microvessels in which the grafted material is particulate, typically as small as about 50 $\mu$m in diameter, preferably about 200 $\mu$m, and larger and contained in a porous vessel that retains the particles but permits passage of the exterior medium. A tag may be included in the microvessel (see, e.g., International PCT application No. WO 96/36436).

2. Combinatorial Libraries, other Libraries and Screening Methodologies

The combinations of matrices with memories are applicable to virtually any synthetic scheme, library preparation or screening protocol. See, especially the applications of matrices with memories described in International PCT application No. WO 97/12680 and WO 96/36436.

a. "Pin" Technology

The applications include those discussed herein, and also methodologies and devices, such as the Chiron "pin" technology (see, e.g., International PCT application No. WO 94/11388; Geysen et al. (1985) *Proc. Natl. Acad. Sci. U.S.A.* 82:178; Geysen et al. (1987) *J. Immunol. Meth.* 102:259–274; Maeji et al. (1994) *Reactive Polymers* 22:203–212), which relies on a support composed of annular synthesis components that have an active surface for synthesis of a modular polymer and an inert support rod that is positioned axially to the annular synthesis components. This pin technology was developed for the simultaneous synthesis of multiple peptides. In particular, the peptides are synthesized on polyacrylic acid grafted on the tip of polyethylene pins, typically arranged in a microtiter format. Amino acid coupling is effected by immersing the pins in a microtiter plate. The resulting peptides remain bound to the pins and can be reused. For purposes herein, the "pins", "crowns" and/or "stems" are radiation grafted using the methods herein, and, are preferably formed from a fluoropolymer or fluoroelastomer.

As provided herein, "pins", including CHIRON CROWNS™ and STEMS™ may be linked to a memory or recording device, preferably encasing the device, or each pin may be coded and the code and the identity of the associated linked molecule(s) stored in a remote memory. As a result it will not be necessary to physically array the pins, rather the pins can be removed and mixed or sorted.

b. Scintillation Proximity Assays (SPAs) and Scintillant-containing Matrices with Memories Scintillation proximity assays are well known in the art [see, e.g., U.S. Pat. No. 4,271,139; U.S. Pat. No. 4,382,074; U.S. Pat. No. 4,687,636; U.S. Pat. No. 4,568,649; U.S. Pat. No. 4,388,296; U.S. Pat. No. 5,246,869; International PCT Application No. WO 94/26413; International PCT Application No. WO 90/03844; European Patent Application No. 0 556 005 A1; European Patent Application No. 0 301 769 A1; Hart et al. (1979) *Molec. Immunol.* 16:265–267; Udenfriend et al. (1985) *Proc. Natl. Acad. Sci. U.S.A.* 82:8672–8676; Nelson et al. (1987) *Analyt. Biochem* 165:287–293; Heath, et al. (1991) *Methodol. Surv. Biochem. Anal.* 21:193–194; Mattingly et al. (1995) *J. Memb. Sci.* 98:275–280; Pernelle (1993) *Biochemistry* 32:11682–116878; Bosworth et al. (1989) *Nature* 341:167–168; and Hart et al. (1989) *Nature* 341:2651]. Beads [particles] and other formats, such as plates and membranes have been developed.

SPA assays refer to homogeneous assays in which quantifiable light energy produced and is related to the amount of radioactively labelled products in the medium. The light is produced by a scintillant that is incorporated or impregnated or otherwise a part of a support matrix. The support matrix is coated with a receptor, ligand or other capture molecule that can specifically bind to a radiolabeled analyte, such as a ligand.

c. Memories with Matrices for Non-radioactive Energy Transfer Proximity Assays

Non-radioactive energy transfer reactions, such as FET or FRET, FP and HTRF assays, are homogeneous luminescence assays based on energy transfer are carried out between a donor luminescent label and an acceptor label [see, e.g., Cardullo et al. (1988) *Proc. Natl. Acad. Sci. U.S.A.* 85:8790–8794; Peerce et al. (1986) *Proc. Natl. Acad. Sci. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/012251]. The donor label is usually a rare earth metal cryptate, particularly europium trisbipyridine diamine [EuTBP] or terbium trisbipyridine diamine [TbTBP] and an acceptor luminescent, presently fluorescent, label. When the donor is EuTBP, the acceptor is preferably allopycocyanin [APC], allophycocyanin B, phycocyanin C or phycocyanin R, and when the donor is TbTBP, the acceptor is a rhodamine, thiomine, phycocyanin R, phycoerythrocyanin, phycoerythrin C, phycoerythrin B or phycoerythrin R.

Energy transfer between such donors and acceptors is highly efficient, giving an amplified signal and thereby improving the precision and sensitivity of the assay. Within distances characteristic of interactions between biological molecules, the excitation of a fluorescent label (donor) is transferred non radiatively to a second fluorescent label (acceptor). When using europium cryptate as the donor, APC, a phycobiliprotein of 5 kDa, is presently the preferred acceptor because it has high molar absorptivity at the cryptate emission wavelength providing a high transfer efficiency, emission in a spectral range in which the cryptate signal is insignificant, emission that is not quenched by presence of sera, and a high quantum yield. When using $Eu^{3+}$ cryptate as donor, an amplification of emitted fluorescence is obtained by measuring APC emission.

The rare earth cryptates are formed by the inclusion of a luminescence lanthanide ion in the cavity of a macropolycyclic ligand containing 2,2'-bipyridine groups as light absorbers [see, e.g., U.S. Pat. No. 5,162,508; U.S. Pat. No. 4,927,923; U.S. Pat. No. 5,279,943; and International PCT Application No. WO 92/012251]. Preferably the $Eu3^+$ trisbypryidine diamine derivative, although the acceptor may be used as the label, is cross-linked to antigens, antibodies, proteins, peptides, and oligonucleotides and other molecules of interest.

For use herein, matrices with memories are prepared that incorporate either the donor or, preferably the acceptor, into or on the matrix. In practice, as with the scintillating matrices with memories, the matrices may be of any format, i.e. particulate, or continuous, and used in any assay described above for the scintillating matrices. For example, the recording device is coated with a protective coating, such as glass or polystyrene. If glass it can be etched. As with preparation of the scintillating matrices with memories, compositions containing the donor or preferably acceptor, such as APC, and typically a polymer or gel, are coated on the recording device or the device is mixed with the composition to produce a fluorescing matrix with memory. To make these matrices resistant to chemical reaction, if needed, they may be coated with polymers such as polyvinylbenzene or polystyrene. Molecules, such as the constituents of combinatorial libraries, are synthesized on the fluorescing matrices with memories, or molecules or biological particles are linked thereto, the identity of the synthesized molecules or linked molecules or biological particles is encoded in memory, and the resulting matrices with memories employed in any suitable assay, including any of those described for the scintillating memories with matrices. In particular, these homogeneous assays using long-lived fluorescence rare earth cryptates and amplification by non radiative energy transfer have been adapted to use in numerous assays including assays employing ligand receptor interaction, signal transduction, transcription factors (protein-protein interaction), enzyme substrate assays and DNA hybridization and analysis [see, Nowak (1993) *Science* 270:368; see, also, Velculescu et al. (1995) *Science* 270:484–487, and Schena et al. (1995) *Science* 270:467–470, which describe methods quantitative and simultaneous analysis of a large number of transcripts that are particularly suited for modification using matrices with memories]. Each of these assays may be modified using the fluorescing matrices with memories provided herein.

For example, a receptor will be labeled with a europium cryptate [where the matrices with memories incorporate, for example allophycocyanin (APC)] or will be labeled with APC, where the matrices incorporate a europium cryptate. After mixing receptor and mixtures of matrices with different ligands, the mixture is exposed to laser excitation at 337 nm, and, if reaction has occurred, typical signals of europium cryptate and APC over background are emitted. Measurement with an interference filter centered at 665 nm selects the signal of the APC labeled receptor from that of europium cryptate labeled ligand on the beads. If particulate, the memories of matrices that emit at 665, can be queried to identify linked ligands.

The following examples are included for illustrative purposes only and are not intended to limit the scope of the invention.

EXAMPLE 1

A. Radiation Grafting

Teflon tubes (19 mm, long, OD: 5 mm, ID: 2 mm; see FIGS. 6C and 6D) were radiation grafted. it was found that dilution of styrene with methanol enhances the rate of grafting. Dilutions of from 5% to 70% were tested. The PTFE tube has the highest styrene grafting at a 50% dilution. The TEFLON® (PTFE) tube is radiated under $^{60}Co$ source at a dose rate of $0.1\times10^6$ rad/h; the total dose of $2.6-2.9\times10^6$ rad.

Functionalization was performed using N-(hydroxymethyl) phthalimide, with trifluoromethane-sulfonic acid (TFMSA) as a catalyst. The polystyrene grafted PTFE tube is thoroughly washed before use to remove residual monomer, non-attached polystyrene and additives remaining from radiation grafting. The amidoalkylation proceeds smoothly in the 50% (v/v) trifluoroacetic acid-dichloromethane solvent at room temperature for 24 hours. The predetermined loading can be obtained by changing the concentrations of reagent, catalyst and reaction time. The hydrazinolysis in refluxing ethanol gives the aminomethyl polystyrene grafted PTFE tube.

FIG. 6 depicts the protocol for radiation grafting of polymers to the surface of TEFLON® (or other suitable surface). FIG. 6C depicts the preparation of a tubular devices in which the matrix is the radiation grafted PTFE and the memory is a transponder, such as the monolithic device, the BMDS transponder (Bio Medic Data Systems, Inc. ("BMDS"), Maywood, N.J.; see, also U.S. Pat. Nos. 5,422,636, 5,420,579, 5,262,772, 5,252,962 and 5,250,962) or IDTAG™ transponder (particularly the IDT150 read/write transponder; ITDAG™ Ltd. Bracknell, Berks RG12 3XQ, UK, fabricated using standard procedures and the method for coil winding, bonding and packaging described in International PCT application Nos. WO95/33246, WO95/16270, WO94/24642, WO93/12513, WO92/15105, WO91/16718; see, also U.S. Pat. Nos. 5,223,851, 5,261,615 and 5,281,855); and FIG. 6D depicts the small chip (2 mm×2 mm×0.1 mm) encased in a radiation grafted polypropylene or teflon ball (or bead, conical tube or other such geometry) with a screw cap or snap on lid. These devices may have removable lids, such as a snap on lid, preferably a snap on lid, or a screw top, so that the memory device can be removed and reused, and can be added after radiation grafting. Loading on the grafted tubes and balls is adjustable and was typically about $0.5\times15$ μmol per tube. The amount can be varied by altering the size of the tube or balls. A variety of selected functional groups are available. Any known to those of skill in the art may be used, including any described herein. PTFE devices are particularly suitable for high temperature reactions (loading was less than or about 3 μmol per device).

B. Protocol for Increasing the Level of Grafting on Fluoropolymer

Dilution of styrene with methanol enhances the rate of grafting. In the radiation-induced grafted copolymerization of styrene to ETFE and TEFLON® (PTFE) tubes (21 mm long, OD: 6 mm, ID: 4 mm), dilutions of from 5% to 70% were tested. The PTFE tube had the highest styrene grafting at a 50% dilution. By adding a mineral acid such as sulfuric acid and nitric acid (concentrations from 0.01–0.5 M), the polystyrene grafting was increased. See Table below. The level of grafting was further improved by machining the ETFEIPTFE tubes from rods rather than extruding the tubes from ETFE/PTFE resin beads at high temperatures. The machined tubes, which as a result of the crimping introduced by machining are about 4 mm shorter than the extruded tubes, have more rough surfaces than the extruded tubes.

| Sulfuric Acid (M) | Polystyrene amount (mg) grafted per tube | | |
|---|---|---|---|
| | extruded ETFE tube | machined PTFE tube | machined ETFE tube |
| 0 | 17 | 10 | 19 |
| 0.05 | — | 12 | 32 |
| 0.1 | 38 | 24 | 48 |
| 0.2 | — | 38 | 56 |

In addition, adjusting the styrene concentration in combination with the use of acid increased the level of grafting. The best increase was observed at a concentration of about 45% styrene in methanol. At 45% styrene grafted in the presence of acid, the amount of polystyrene grafted per tube was almost 70 mg, compared to less than about 20 mg grafted in the absence of acid. At other concentrations of styrene in acid the amount grafted varied from about 30 mg to the high of 70 mg. In the absence of acid, grafting is substantially independent of styrene concentration for the tested concentration range (25% to 50%).

The amount of polystyrene grafted onto PTFE and ETFE is increased when the fluoropolymer is machined prior to radiation grafting. Furthermore, grafting of the machined fluoropolymer in the presence of acid provides still higher levels of grafting. In general, the level of grafting is greater than 10 mg, usually greater that 12 mg, often greater that 15 mg, sometimes greater than 20 mg, occasionally greater than 40 mg, and as high as 50 mg, of polystyrene per 320 $mm^2$ of fluoropolymeric surface area.

| Fluoropolymer (320 $mm^2$ surface area) | Amount of polystyrene (mg) grafted | | |
|---|---|---|---|
| | without machining or acid | with machining | with machining and acid |
| PTFE | <10 | 17 | 28 |
| ETFE | <10 | 19 | 50 |

Functionalization of the grafted copolymer was performed as described above, using N-(hydroxymethyl) phthalimide, with trifluoromethanesulfonic acid as catalyst. The polystyrene-grafted PTFE tube was thoroughly washed before use to remove residual monomer, non-attached polystyrene and additives remaining from radiation grafting. The amidoalkylation proceeded smoothly in 50% (v/v) trifluoroacetic acid-dichloromethane as the solvent at room temperature for 24 hours.

A predetermined loading can be obtained by changing the concentrations of reagent, catalyst and reaction time. The hydrazinolysis in refluxing ethanol gave an aminomethyl polystyrene grafted PTFE or ETFE tube. The loading of amine groups on a PTFE tube was about 41 $\mu$mol, and on an ETFE tube was as high as 52 $\mu$mol.

The two modifications to the procedure using acid and also machining the polymer substantially increased polystyrene radiation grafting levels. Adding a an acid, particularly mineral acid such as sulfuric or nitric (concentrations 0.01 M to 0.5 M) increased the grafted polystyrene from about 20 to 200%. Using a rough surface further increased the level of grafting.

EXAMPLE 2

Radiation Grafting of a Polymer on an Inert Surface for Preparation of Matrices with Memories Matrices for use as supports for synthesis and for use in coupled (single platform) protocols have been prepared using radiation grafting. These supports include any inert surface, including PTFE (TEFLON®), which heretofore does not appear to have been used for radiation grafting. The methods exemplified below with reference to FIGS. 6 have been designed for use with PTFE as well as other surfaces. A method of radiation-induced grafted copolymerization of styrene to TEFLON® (PTFE) has been developed.

A. FIG. 6A

1. Preparation of Polymer

Figure 6A:
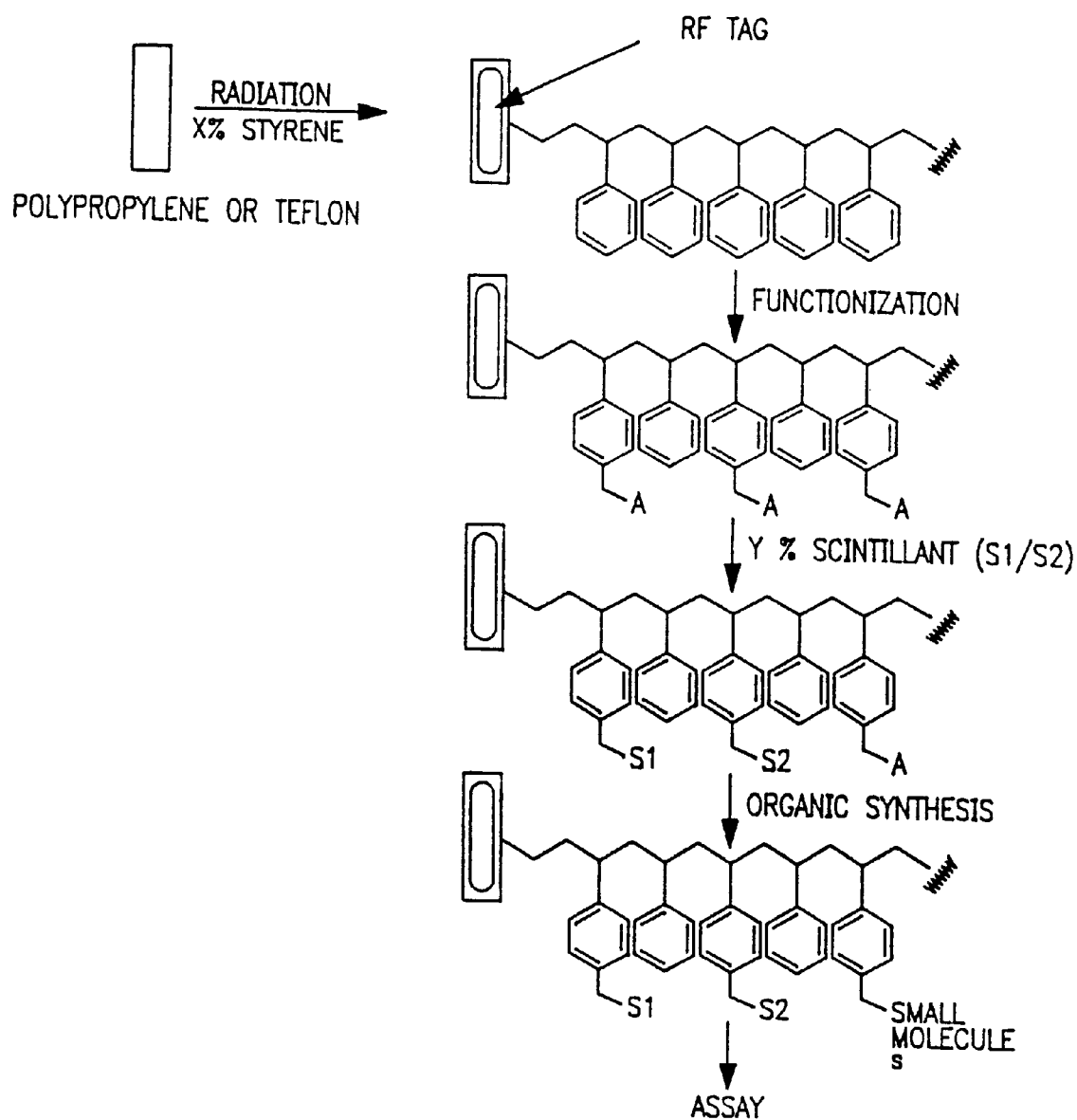

FIG. 6A schematically shows the preparation of polymer. Polystyrene is radiation grafted onto polypropylene or TEFLON® tubes, an RF tag, such as the BMDS tag, or IDTAG transponder, was inserted into the tube to produce the microreactor. The polystyrene is then functionalized with selected functional groups (i.e., such as "A" in FIG. 6A). Scintiliant is covalently linked onto the polystyrene though "A", and a bioactive molecule, such as, for example, biotin, can be synthesized on the surface using the remaining "A" functionalities. The grafting of the fluoropolymer is effected using acid and/or prior roughening of the surface. Grafting of other polymers is preferably effected using roughening or both roughening and grafting in acid.

2. Radiation

The TEFLON® (PTFE) tube was radiated under a $^{60}$Co source at a dose rate of $0.1 \times 10^6$ r/h; the total dose is typically $2.6$–$2.9 \times 10^6$ r.

3. Polymers

Using radiation-induced grafting polymerization techniques, a variety of monomers such as styrene, acrylic acid, methylacrylic acid, 2-hydroxymethylacrylate, and other such monomers are used to produce different polymeric surfaces with different functional groups on polypropylene (PP), polyethylene (PE) and fluoropolymers. Polyethylene oxide (PEG) may be grafted onto the surface to change the hydrophilicity and reduce the steric-hinderance to antibodies or receptors. Functional groups such as amines, alcohols and phenols, carboxylic acids, halides, aldehydes, nitrites and other such groups can be introduced.

It was found that dilution of monomers, such as styrene, with methanol enhanced the rate of grafting. PP and PTFE tubes have demonstrated highest styrene grafting at styrene concentrations of about 25 to 50%.

4. Functionalization

The functionalization was performed using the readily available N-(hydroxymethyl)phthalimide, with trifluoromethanesulfonic acid as catalyst. The polystyrene grafted tubes are thoroughly washed before use to remove residual monomer, non-attached polystyrene and additives remaining from radiation grafting. The amidoalkylation proceeds smoothly in 50% (v/v) trifluoroacetic acid-dichloromethane as solvent at room temperature for 24 hours. A predetermined loading can be obtained by changing the concentrations of reagent, catalyst and reaction time. The hydrazinolysis in refluxing ethanol gives the aminomethyl polystyrene grafted PTFE tube.

The microreactors were prepared in different sizes (2–12 mm) with loading capacity range from 0.5–15 pmol per tube.

5. Fluorophores

The scintillants, which are chemically stable, were chosen to match the energy gap from radiation energy of radioisotopes. Scintillants such as 9-anthracenepropionic acid, 1-pyrenebutanoic acid and their derivatives are matched to the energy transfer for different radioisotopes, in including $^{125}$I, $^{3}$H, $^{14}$C and others. Care should be taken when selecting combinations of scintillants and radioisotopes so that energy transfer from isotope to scintillant is matched.

A portion of the functional groups were covalently linked to the mixture of primary fluor (S1, molecules that emit light following interaction with radiation) and secondary fluor (S2, wavelength shifter). Experiments were performed with mixture of S1/S2 at the ratio ranging from 20:1 to 100:1 for S1 and S2 respectively, with optimum ratio of 40:1 for most of the experiments presented here. Conditions in which 20% to 80% of the functional groups were occupied with mixture of S1/S2 were evaluated. The optimum number of the functional groups linked to primary and secondary fluors for most of the experiments was 50%.

The remaining of the functional groups (20% to 80%) were used for chemical synthesis. Small molecules (e.g., biotin) were synthesized on the solid support as described in Example 2.B. (see FIG. 6B).

6. Chemical synthesis on the surface of microreactors

A variety of small molecules, such as biotin, peptides, and oligonucleotides, may be synthesized on microreactors (see, e.g., Example 2.B. and FIG. 6B (biotin), below). In order to reduce steric hinderance and improve the interaction of labeled biological target (e.g., antibody, receptor, complementary DNA or RNA, labeled probe), and depending on the size and nature of the small molecule, different percentages of the functional groups were used for chemical synthesis while the remaining functional group(s) were blocked with Boc. Conditions in which 0.25% to 100% of the functional groups were used for chemical synthesis were evaluated. The results indicated that use of 25% of the functional groups for chemical synthesis is optimal.

B. Biotin Synthesis

Figure 6B:
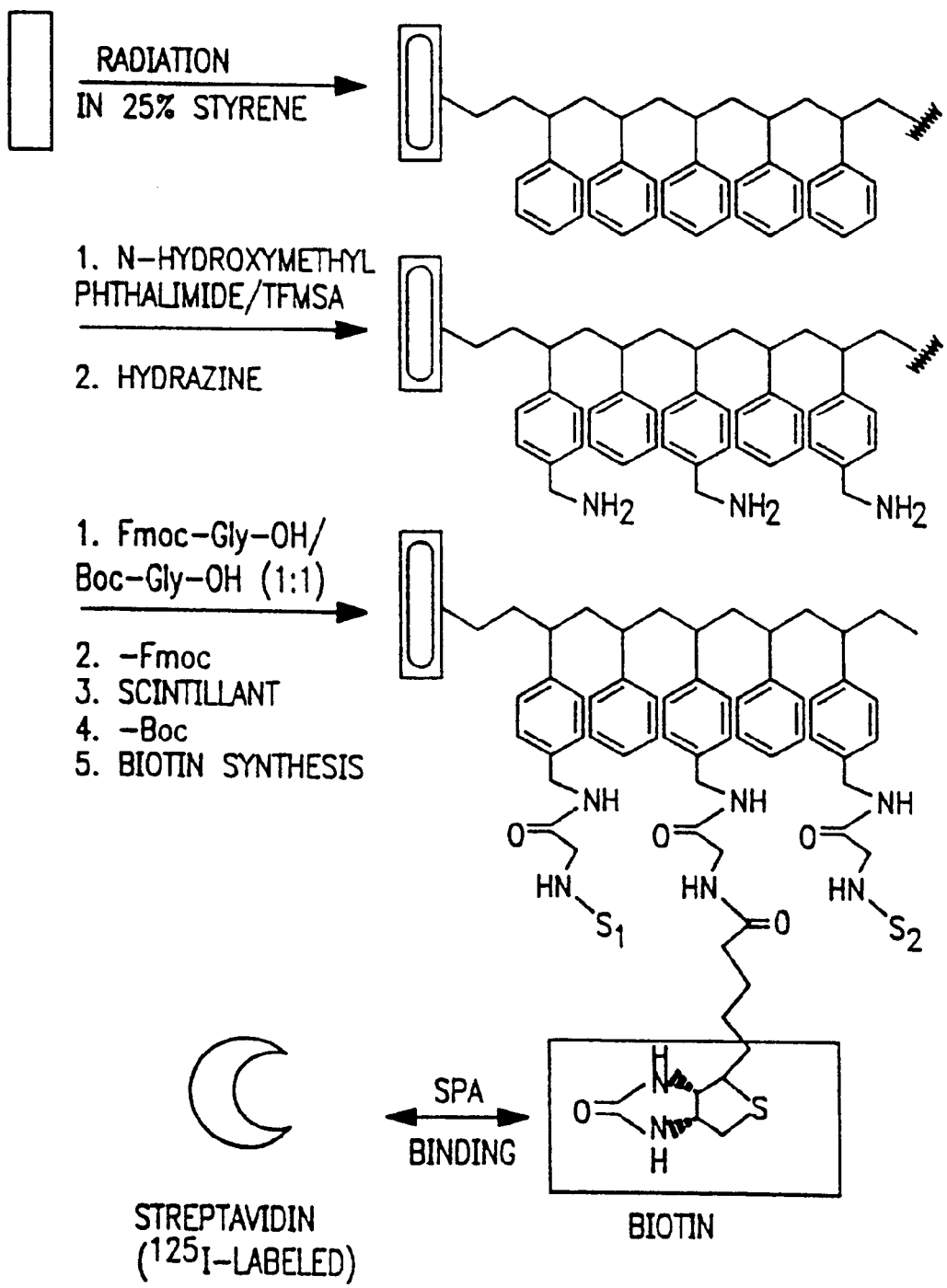
Figure 6C:
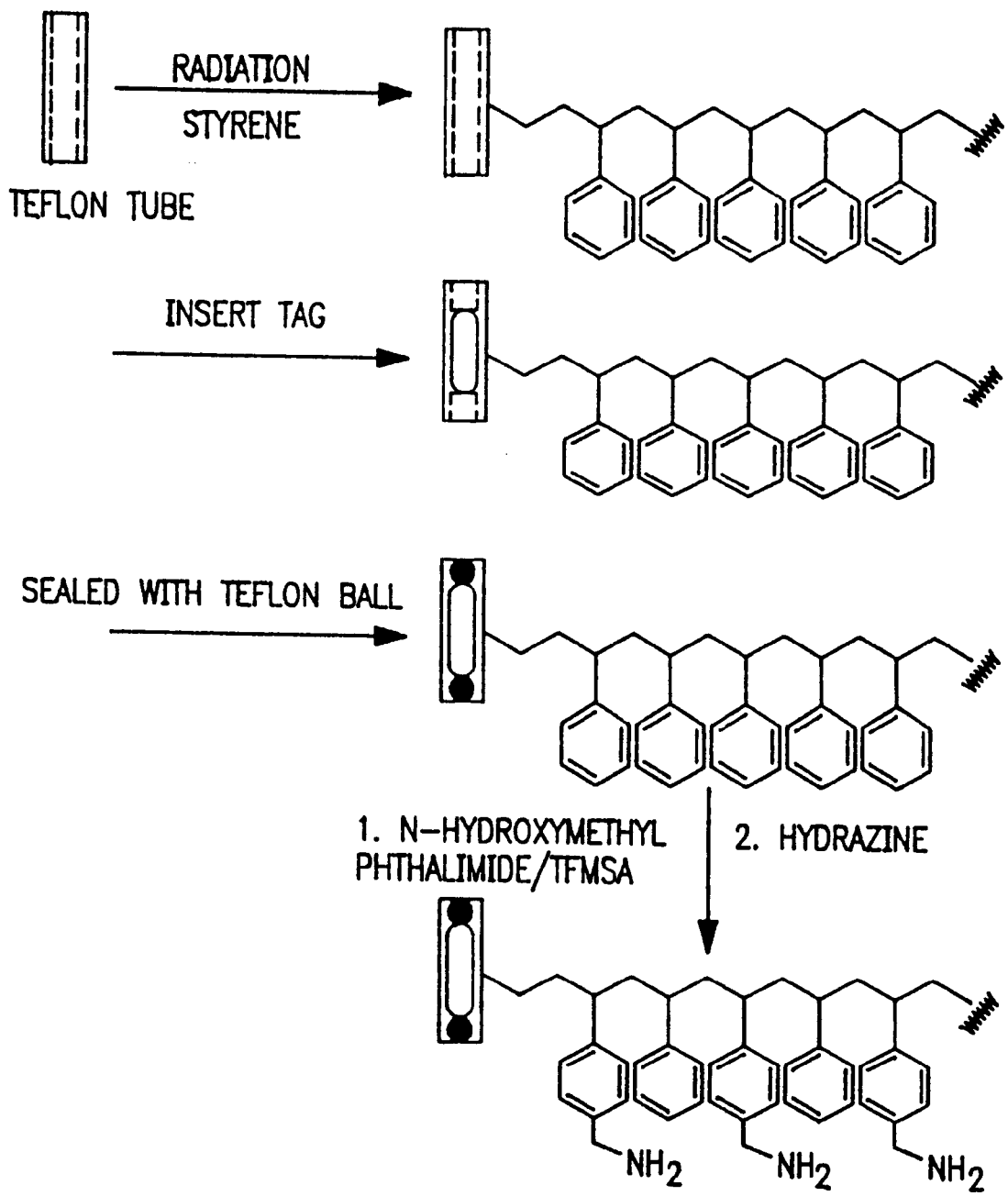
Figure 6D:
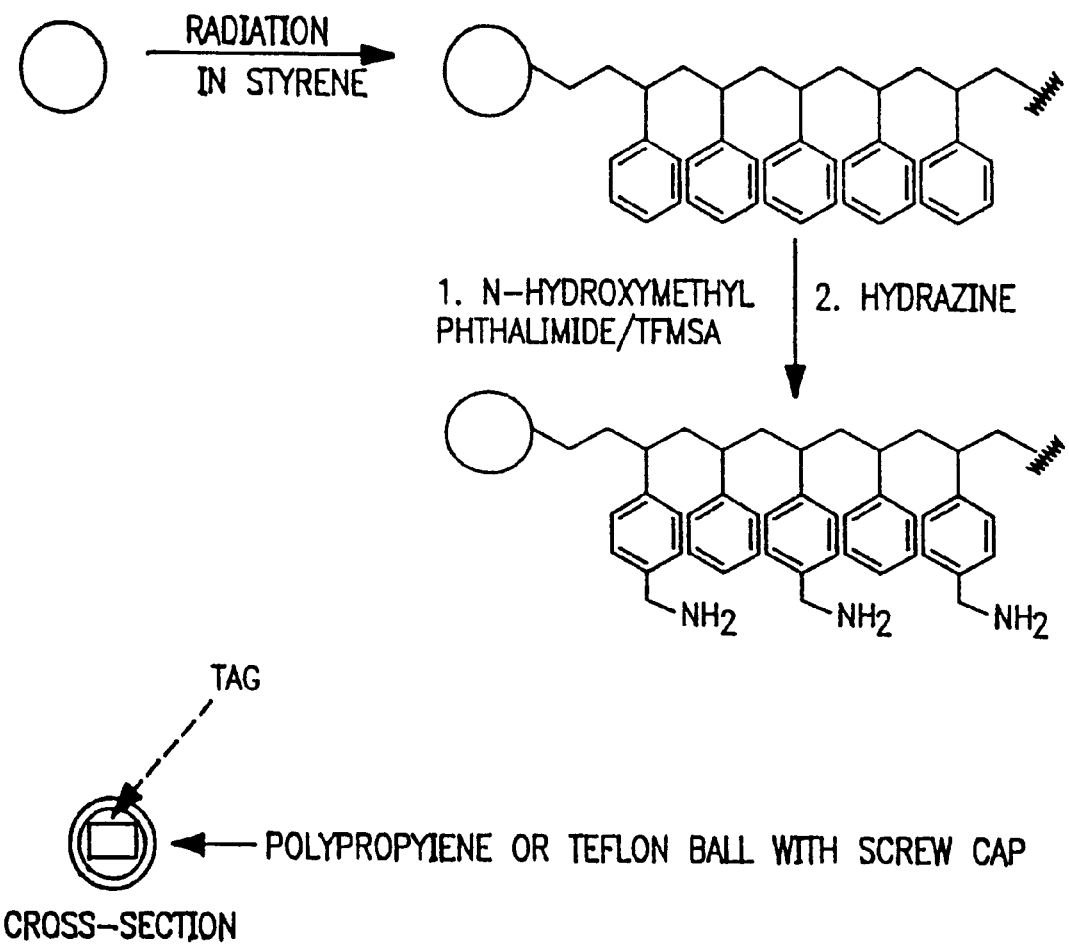

Biotin synthesis is shown in FIG. 6B. In order to reduce steric hinderance and improve the interaction of labeled biological target (e.g., $^{125}$I-receptor), and depending on the size and nature of the small molecule, a different percentage of the functional groups was utilized for chemical synthesis, while the remaining functional group were blocked with Boc. The experiments indicate that optimum results are obtainable with 25% of the functional group dedicated for chemical synthesis.

1. Synthesis

Fmoc (Fmoc-Gly-OH) and Boc (Boc-Gly-OH) linked amino acids were used to control the loading of scintillants and remaining amines. The Fmoc groups were removed using 20% piperidine in DMF, and Boc groups were removed using a 1:1 ratio of TFA and dichloromethane. About 50% of the amine groups were covalently linked to scintillants. The remaining 50% of the amine groups were used to synthesize biotin.

2. Assays

The activity of molecules synthesized on the surface of the microvessels may be evaluated in a variety of solid based assay formats.

a. SPA Assay

The biological activity of small molecules synthesized on the surface of the tubular matrices with memories may be evaluated in a variety of scintillation proximity assay formats as described herein. For example, biotin and its derivative (2-imidazolidone-4-carboxylic acid) were synthesized on the tube and the binding characteristics of the synthesized molecules on the solid support to $^{125}$I-streptavidin in a scintillation proximity assay (SPA) were evaluated. The results demonstrated that the biotin derivative, 2-imidazolidone-4-carboxylic acid, has much lower affinity for streptavidin as evidenced by exhibition of a lower signal.

b. ELISA Type Assay

ELISAs can be performed using antibodies to small molecules, such as a peptide. For example metenkephalin was synthesized on a microreactor, and anti-metenkephalin antibody was used. As an example of a nonpeptide small molecule, biotin was synthesized and an anti-biotin antibody labeled with alkaline phosphatase was used to detect by colorimetric, fluorometric or luminescent means.

c. Radio-immunoassay

Using radio-labeled antibody or receptor, a variety of radio-immunoassays may be designed using the microreactors.

d. Detection of Oligonucleotides

A variety of the labeled probes (e.g., fluorescence and radiolabels) may be used to detect the identity of a synthesized oligonucleotide on the surface of the polymer, which has been radiation grafted (see above) on a icroreactor. Oligonucleotides may also be characterized using a labeled omplementary DNA or RNA in a hybridization assay.

EXAMPLE 3

Wash and SPA Assay Procedure Using the Microreactors

1. Covalently Linking Scintillant to the Surface of the Microreactor

Scintillants (pyrenebutyric acid and 9-anthracenepropionic acid) were covalently linked to the grafted polystyrene on the surface of the polymer. The fluorophore was linked to 50% of the available functional groups as described above (see Example 2.A.5.).

2. Synthesizing Biotin on the Microreactor

The remaining 50% of functional amine groups on the surface of the MICROTUBE™ microreactor was estimated by Fmoc derivatization, cleavage and quantitation of the resulting chromophore to be ~1.8 µmol/tube. The amine group was covalently linked to biotin under conditions described as follows: 0.012 M biotin, 0.024 M DIEA (diisopropylethylamine), 0.012 M PYBOP (benzotriazol-1-yl-oxy-tris-pyrrolidino-phophonium hexafluorophosphate) in DMF (N,N-dimethyl formamide) at room temperature for 1 hour.

3. Washing Protocol for the Microreactors

A. Development and Optimization of Wash Procedure

The microreactors were washed with various detergents (SDS, CHAPS (3-((3-cholamidopropyl)dimethylammonio)-1-propanesulfonate, Triton X-100, or Benzalkonium Chloride) or charcoal. The effects of detergents were evaluated by washing the microreactors with different concentrations of detergents (0.5 to 5% in PBS) for 24 hours on an orbital shaker at room temperature. The charcoal wash was done by dialysis against PBS containing 10–35% charcoal (4–8 mesh).

It was found that the microreactors that had been washed with SDS, Benzalkonium Chloride or charcoal had an improved signal to noise ratio. Additional wash studies were performed with either SDS and/or charcoal in wash buffer. The effect of SDS concentration was assessed by washing the tube with 0.25, 0.5, 0.75, or 1% SDS in PBS for 24 hours. Results of this experiment indicated that microreactors that had been washed with 0.5%–0.75% SDS and/or charcoal in PBS yielded a better signal to noise ratio.

Finally, the optimal wash period was determined by washing microreactors with 0.75% SDS/charcoal for 1, 2, 3, 4, or 5 days at room temperature on an orbital shaker. The results of this experiment revealed that washing tubes for 2 days efficiently removes undesirable material which interfere with the SPA signal.

B. Optimized Wash Procedure

After synthesis of small molecules (biotin), the microreactors were washed as described above. The microreactors were placed in a dialysis bag and were dialyzed against PBS containing 0.75% SDS, with or without 35% charcoal, for 2 days at room temperature on an orbital shaker. At the end of SDS wash, microreactors were rinsed with PBS (10 mL/microreactor) two times.

Thus, performance of assays on solid supports can be improved by washing the solid support with linked biological particle or molecule with 0.75% SDS with or without 35% charcoal in PBS (pH 7.2) for about 2 days.

4. Blocking

The microreactors were placed in PBS (pH 7.2) buffer containing 3% BSA (bovine serum albumin) and incubated overnight at 4° C.

5. SPA Detection.

Biotin was detected in the SPA format. Microreactors were placed in 24 well plate containing 1 mL of Assay Buffer (10 mM Sodium Phosphate pH 7.2, 150 mM NaCl, 0.5% BSA, 0.05% Tween 20, and 125I-streptavidin (244 ng/mL, specific activity 0.291 $\mu Ci/\mu g$)). Microreactors were incubated at room temperature on an orbital shaker for 2 hours. The extent of 125I streptavidin binding on the Microreactors was assessed in a Wallace MicroBeta Trilux scintillation counter.

Since modifications will be apparent to those of skill in this art, it is intended that this invention be limited only by the scope of the appended claims.

What is claimed is:

1. A solid support for use in chemical synthesis comprising:
   a graft polymer radiation grafted onto a surface of a fluoropolymer, wherein the fluoropolymer comprises a material that is resistant to temperatures present during chemical synthesis and wherein the radiation grafting is effected in a solution of the graft polymer, methanol and an acid.

2. The solid support of claim 1, wherein the acid is a mineral acid.

3. The solid support of claim 1, wherein the fluoropolymer comprises polytetrafluoroethylene or ethylene-tetrafluoroethylene copolymer.

4. The solid support of claim 1, wherein the fluoropolymer is formed as a tube.

5. The solid support of any of claim 4, wherein the exterior of the tube is imprinted with an optically-readable symbol.

6. The solid support of claim 4, wherein a radiofrequency tag is disposed within the tube subsequent to radiation grafting.

7. The solid support of claim 1, wherein the fluoropolymer is formed as a solid body.

8. The solid support of claim 7, wherein the surface of the solid body is imprinted with an optically-readable symbol.

9. The solid support of claim 7, wherein a radiofrequency tag is embedded within the solid body.

10. The solid support of claim 1, wherein the graft polymer is a styrene.

11. The solid support of claim 10, wherein the styrene is a polystyrene.

12. The solid support of claim 4, wherein the solid support exhibits loading within the range of 0.5–15 $\mu$mol per tube.

13. The solid support of claim 1, wherein the surface is mechanically roughened prior to radiation grafting.

* * * * *